(12) United States Patent
Hutchinson et al.

(10) Patent No.: US 9,366,655 B2
(45) Date of Patent: Jun. 14, 2016

(54) METHOD FOR ULTRASONIC INSPECTION OF IRREGULAR AND VARIABLE SHAPES

(75) Inventors: Michael C. Hutchinson, Kent, WA (US); James C. Kennedy, Renton, WA (US); Barry A. Fetzer, Renton, WA (US); Michael Joseph Duncan, Lake Tapps, WA (US); Navpreet S. Grewal, Redmond, WA (US); Steven Ray Walton, Wilkeson, WA (US); Hien T. Bui, Kent, WA (US)

(73) Assignee: The Boeing Company, Chicago, IL (US)

( * ) Notice: Subject to any disclaimer, the term of this patent is extended or adjusted under 35 U.S.C. 154(b) by 796 days.

(21) Appl. No.: 13/532,815

(22) Filed: Jun. 26, 2012

(65) Prior Publication Data

US 2013/0340531 A1    Dec. 26, 2013

(51) Int. Cl.
   *G01N 29/26* (2006.01)
   *G01N 29/11* (2006.01)

(52) U.S. Cl.
   CPC .............. *G01N 29/11* (2013.01); *G01N 29/262* (2013.01); *G01N 2291/2638* (2013.01)

(58) Field of Classification Search
   CPC ..... G01N 29/11; G01N 29/06; G01N 29/069; G01N 29/4409; G01N 29/4427; G01N 29/48; G01N 29/34; G01N 29/341; G01N 29/343; G01N 29/346; G01N 29/262; G01N 2291/2638
   USPC ........... 73/602, 633, 640, 641, 621, 625, 626, 73/628
   See application file for complete search history.

(56) References Cited

U.S. PATENT DOCUMENTS

| | | |
|---|---|---|
| 6,722,202 B1 | 4/2004 | Kennedy et al. |
| 6,993,971 B2 | 2/2006 | Bossi et al. |
| 7,231,826 B2 | 6/2007 | Bossi et al. |
| 7,249,512 B2 | 7/2007 | Kennedy et al. |

(Continued)

FOREIGN PATENT DOCUMENTS

| | | |
|---|---|---|
| DE | 102008002450 A1 | 10/2009 |
| EP | 2249152 A2 | 11/2010 |
| WO | 2009124916 A3 | 10/2009 |

OTHER PUBLICATIONS

International Preliminary Report on Patentability dated Dec. 31, 2014, International Application No. PCT/US2013/033486 (counterpart of the instant application).

(Continued)

*Primary Examiner* — Daniel S Larkin
*Assistant Examiner* — Rose M Miller
(74) *Attorney, Agent, or Firm* — Ostrager Chong Flaherty & Broitman P.C.

(57) ABSTRACT

System and method for enabling ultrasonic inspection of a variable and irregular shape. The system comprises one or more ultrasonic pulser/receivers, one or more ultrasonic transducer arrays, a shoe or jig to hold and position the array(s), data acquisition software to drive the array(s), and data analysis software to select a respective best return signal for each pixel to be displayed. This system starts with information about the general orientation of the array relative to the part and a general predicted part shape. More specific orientation of the transmitted ultrasound beams relative to the part surface is done electronically by phasing the elements in the array(s) to cover the expected (i.e., predicted) surface as well as the full range of part surface variability.

5 Claims, 14 Drawing Sheets

(56) References Cited

U.S. PATENT DOCUMENTS

| | | |
|---|---|---|
| 7,263,889 B2 | 9/2007 | Kennedy et al. |
| 7,484,413 B2 | 2/2009 | Georgeson et al. |
| 8,402,830 B2 | 3/2013 | Kleinert et al. |
| 8,453,509 B2 | 6/2013 | Oberdorfer et al. |
| 8,678,121 B2 * | 3/2014 | Troy et al. ............ 180/167 |
| 8,763,462 B1 * | 7/2014 | Fetzer et al. ............ 73/623 |
| 2006/0283250 A1 * | 12/2006 | Fair et al. ............ 73/593 |
| 2007/0006657 A1 | 1/2007 | Kennedy et al. |
| 2008/0121040 A1 * | 5/2008 | MacLauchlan ...... G01N 29/265 73/618 |
| 2010/0094606 A1 * | 4/2010 | Richard ............ G01B 17/06 703/2 |
| 2010/0095775 A1 | 4/2010 | Sarr et al. |
| 2012/0024067 A1 | 2/2012 | Oberdoerfer et al. |
| 2012/0310551 A1 * | 12/2012 | Na ............ G01N 29/0645 702/39 |

OTHER PUBLICATIONS

International Search Report dated Apr. 29, 2014, International Application No. PCT/US2013/033486 (counterpart of the instant application).

Machine Translation of DE 10 2008 002450 A1.

* cited by examiner

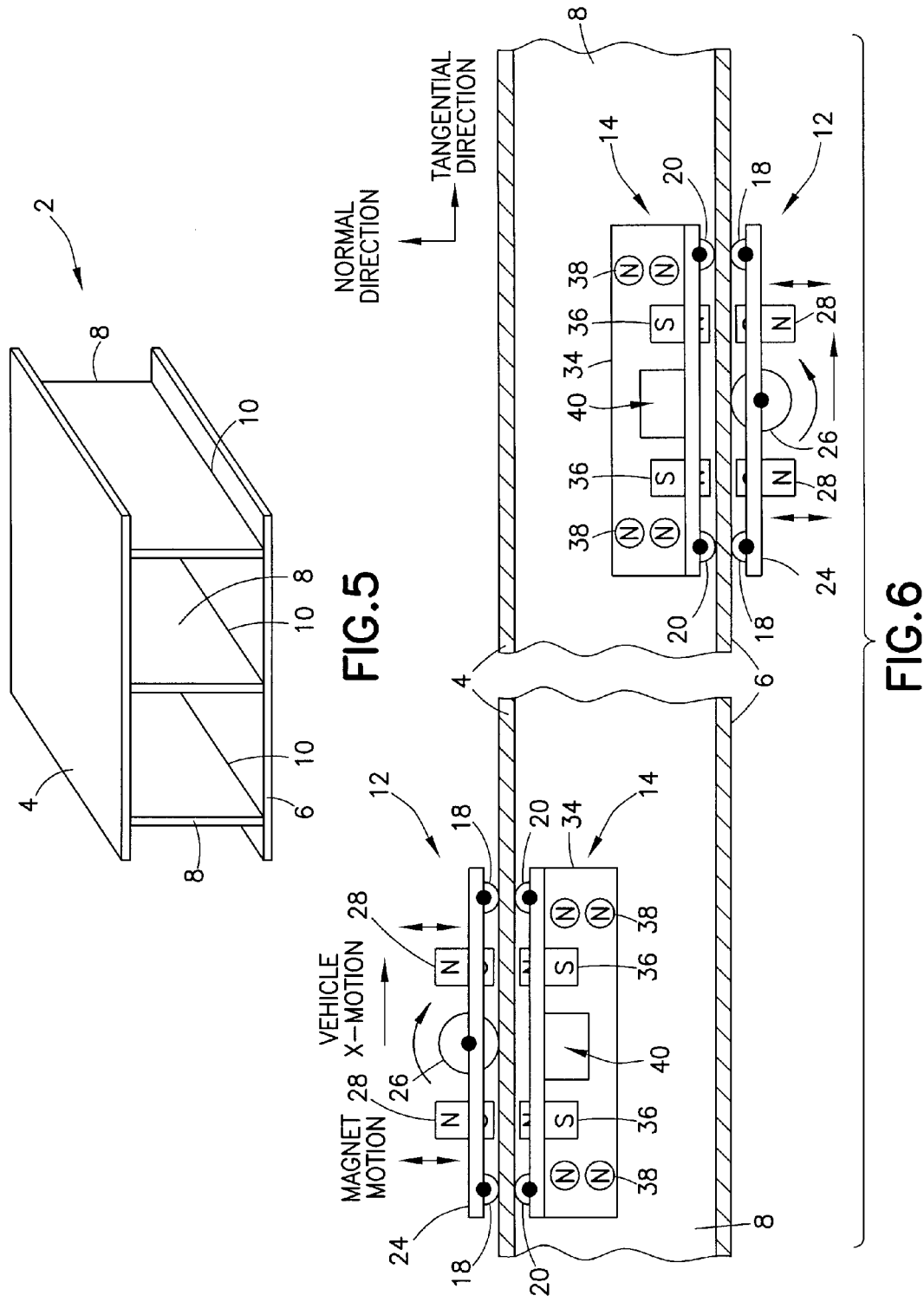

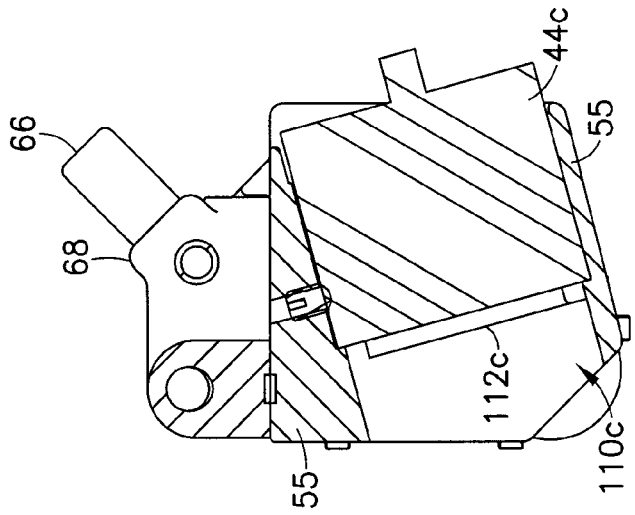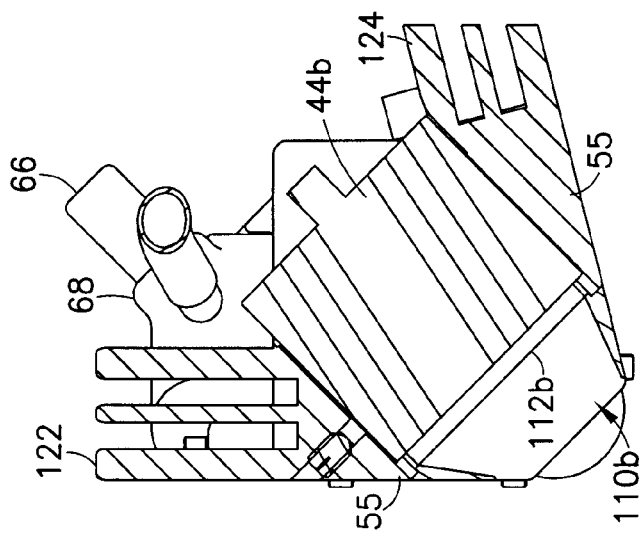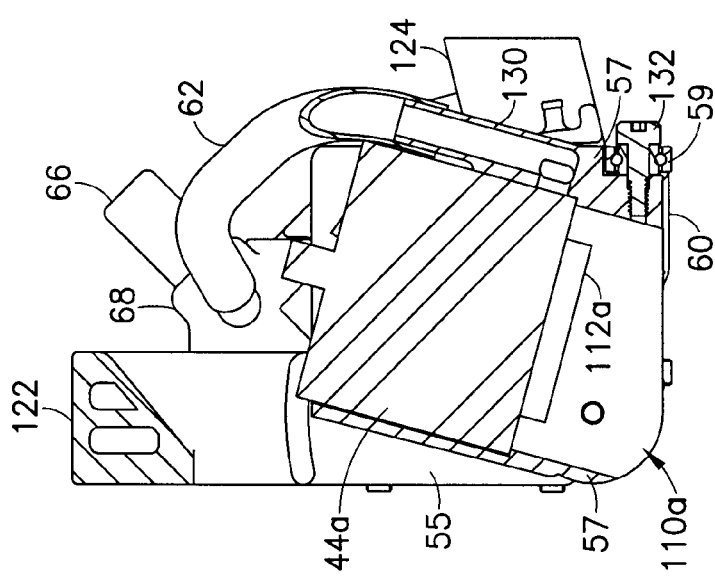

METHOD FOR ULTRASONIC INSPECTION OF IRREGULAR AND VARIABLE SHAPES

BACKGROUND

This disclosure generally relates to inspection equipment and methods, and deals more particularly with methods and apparatus for inspecting structures having irregular and variable shapes, especially soft-tooled structures made of composite material.

A variety of elongated composite structures may have relatively confined internal cavities that require inspection in order to assure that the structure meets production and/or performance specifications. Conventional composite structure cured with hard tooling results in composite radii that are well defined and repeatable. In contrast, the composite radii formed using soft tooling are not always well defined and may vary from part to part. In some cases, dimensional or contour variations may be greater than those that would result from using hard tooling. These larger variations make reliable inspection using conventional methods more challenging. In view of the deviation from circularity of soft-tooled composite radii, the term "radius" as used hereinafter should be construed non-strictly to include non-circular profiles.

Critical composite structure in aerospace and potentially in applications outside aerospace must be inspected to required specifications to ensure structural integrity. Inspecting soft-tooled composite structures presents distinct yet interrelated challenges. Critical inspection areas include the radii. Moreover, such soft-tooled "radii" must be inspected in a production environment. For a production inspection, the inspection rate must be sufficient to meet the part production rate.

For ultrasonic inspection of composite structure, the ultrasound beam should ideally enter at 90 degrees to the local surface of the composite part being inspected. If it does not enter at 90 degrees, it will be refracted off normal and a return echo from any possible internal structure or anomaly will not be optimum. Traditionally a 90-degree entry angle is maintained by holding a sensor array at a precisely fixed position in space relative to the surface. While this works well for known surfaces, such as flat or cylindrical surfaces of a given, fixed radius and circular shape, this approach will not provide adequate results for surfaces which are, for example, parabolic, irregular, or of varying radius of not necessarily cylindrical cross section. Traditional methods of interrogating such a radius with ultrasound fail to keep the sound path sufficiently perpendicular over the entire inspection area.

There is a need for methods and apparatus for inspecting composite structures having internal cavities that allow inspection of soft-tooled radii from inside the cavity. The methods and apparatus must also provide that the sensor energy enters the composite part volume very close to the local perpendicular at the inspection site.

SUMMARY

The system and method disclosed herein enables the ultrasonic inspection of a variable and irregular shape. An example of a primary use of this scanning system would be for the inspection of a variable radius or a noncircular radius produced using soft tooling to form a composite structure, such as an integrally stiffened wing box of an aircraft. The system comprises one or more ultrasonic pulser/receivers, one or more ultrasonic transducer arrays, a shoe or jig to hold and position the array(s), ultrasonic data acquisition application software to drive the array(s), and ultrasonic data acquisition application software to select the best signal for each pixel to be displayed.

The ultrasonic data acquisition/analysis system disclosed herein has the ability to scan a part of variable and irregular shape starting with a general orientation of the array relative to the part and a general predicted part shape. More specific orientation of the transmitted ultrasound beams relative to the part surface is done electronically by phasing the elements in the array(s) to cover the expected (i.e., predicted) surface of the part as well as the full range of part surface variability. The phasing is done in accordance with predetermined focal laws. (As used herein, the term "focal laws" refers to the programmed pattern of time delays applied to pulsing and receiving from the individual elements of a transducer array in order to steer and/or focus the resulting ultrasound beam and echo response.) The ultrasonic data analysis application software then selects the best return signal for each spatial element of the part for display as a pixel and discards other return signals. The disclosed system is able to scan at a fast rate, mechanically simple and robust.

For one specific application involving the inspection of a soft-tooled radius of an integrally stiffened wing box, the above-described ultrasonic data acquisition/analysis system can be integrated into a non-destructive inspection system comprising: an active trailer vehicle that carries the ultrasonic transducer array(s) for inspecting the soft-tooled radius; an external motorized tractor used to move the active trailer vehicle through the tunnels of the wing box; one or more ultrasonic pulser/receivers connected to the ultrasonic transducer arrays; a computer that hosts the ultrasonic analysis, data acquisition and movement control software; and a monitor for displaying C-scan images of the inspected part.

One or more computer programs, i.e., software, running on a computer or other hardware and software system with a processor capable of operating under software control, may be used for acquisition of ultrasonic inspection data by the ultrasonic transducer arrays connected to one or more pulser/receiver devices, and related or combined software may also be used to analyze the received data. Data analysis software interprets the inspection data and maps a C-scan from the probe onto a display monitor for review by an operator, such as a technician performing a scanning operation. For example, the software may combine the inspection data from ultrasonic transducers with position data from an optical encoder with predefined structural data representing the configuration of the structure under inspection, including any position information for discontinuities in the structure, to provide the technician a virtual image of the ongoing non-destructive inspection by the ultrasonic inspection system. Data analysis software may also provide a user with tools for further controlled analysis of the displayed data.

In accordance with one aspect, a method for inspecting a portion of a part having a surface of unknown shape is provided which comprises: (a) electrically pulsing respective groups of transducer elements of an array in accordance with respective focal laws of a first set of focal laws to emit a plurality of focused beams in sequence, the focused beams being directed from different angles toward a target location on the surface; (b) after each respective group of transducers is pulsed, receiving electrical signals from the respective group in accordance with respective focal laws of a second set of focal laws to form a respective return signal representing a respective echo returned to a respective group from the inspected part; (c) processing the return signals to derive respective values of a parameter characterizing the return signals; and (d) selecting one of the respective parameter values that satisfies a first condition. In one embodiment, the parameter can be amplitude and the first condition is having the greatest amplitude. For such an embodiment, the method further comprises displaying a pixel having a value which is a function of at least the selected parameter value.

In another embodiment, the method further comprises: selecting another of the respective parameter values that satisfies the first condition or a second condition; and displaying a pixel having a value which is a function of at least the two selected parameter values. The method further comprises supplying fluid acoustic couplant into a space between the array and the part, wherein step (c) comprises applying respective gains to the respective return signals, the gains being selected to compensate for different amounts of energy loss caused by transmission inefficiency at higher angles. The respective gains being a function of distance of travel of each echo through the fluid acoustic couplant.

In accordance with another aspect, a method for inspecting a portion of a part having a surface of unknown shape is provided which comprises: (a) determining a shape of an inspection zone and a range of variation thereof; (b) determining a position of an ultrasonic transducer array that, when phased, can project focused beams at a plurality of target locations in the inspection zone; (c) determining focal laws for interrogating target locations of inspection zones having shapes which vary within the range of variation using focused beams having different steering angles; (d) positioning the ultrasonic transducer array in the determined position; (e) pulsing the ultrasonic transducer array in accordance with the determined focal laws; (f) forming respective return signals representing respective echoes returned to the ultrasonic transducer array from the inspected part; and (g) selecting a respective parameter value of a respective best return signal for each interrogated target location. The selected parameter values are then displayed as pixels on a display monitor.

In accordance with a further aspect, a method for inspecting a portion of a part having a surface of unknown shape is provided which comprises: (a) positioning an array of transducer elements at a position along an axis with an orientation that allows the array, when phased, to project focused beams which are respectively normal or nearly normal to first and second target locations on the surface, a centerline of the array and the first and second target locations lying in a first plane; (b) while the array is in the position along the axis, electrically pulsing respective groups of transducer elements of the array in sequence using time delays in accordance with a first set of focal laws, which pulsing causes each pulsed group to emit a respective focused beam directed at the first target location at respective steering angles; (c) applying time delays in accordance with the first set of focal laws to form respective return signals from electrical signals output by the respective groups of transducer elements in response to echoes from the first target location following emission of the focused beams directed at the first target location; (d) selecting a first return signal having a characteristic which indicates it corresponds to an emitted beam that was normal or nearly normal to the part surface at the first target location; (e) while the array is in the same position, electrically pulsing respective groups of transducer elements of the array in sequence using time delays in accordance with a second set of focal laws, which pulsing causes each pulsed group to emit a respective focused beam directed at the second target location at respective steering angles; (f) applying time delays in accordance with the second set of focal laws to form respective return signals from electrical signals output by the respective groups of transducer elements in response to echoes from the second target location following emission of the focused beams directed at the second target location; (g) selecting a second return signal having a characteristic which indicates it corresponds to an emitted beam that was normal or nearly normal to the part surface at the second target location; and (h) displaying first and second pixels in a first column, wherein the first pixel has a value which is a function of at least a parameter value of the first return signal, and the second pixel has a value which is a function of at least a parameter value of the second return signal.

Yet another aspect is a method for inspecting a part having a surface, the method comprising: (a) positioning a first array of transducer elements at an axial position along an axis with a first orientation that allows the first array, when phased, to project focused beams which are respectively normal or nearly normal to a first target location on the surface, a centerline of the first array and the first target location lying in a plane; (b) while the array is in the first position, electrically pulsing respective groups of transducer elements of the first array using time delays in accordance with a first set of focal laws, which pulsing causes each pulsed group to emit a respective focused beam directed at the first target location at respective steering angles, the beams being emitted in sequence; (c) applying time delays in accordance with the first set of focal laws to form respective return signals from electrical signals output by the respective group of transducer elements of the first array in response to emission of the focused beams directed at the first target location; (d) selecting a first return signal having a characteristic which indicates it corresponds to an emitted beam that was normal or nearly normal to the part surface at the first target location; (e) after steps (a) through (d) have been performed, positioning a second array of transducer elements at the axial position along the axis with a second orientation different than the first orientation that allows the second array, when phased, to project focused beams which are respectively normal or nearly normal to a second target location on the surface, a centerline of the second array and the second target location lying in the plane; (f) while the second array is in the axial position, electrically pulsing respective groups of transducer elements of the second array in sequence using time delays in accordance with a second set of focal laws, which pulsing causes each pulsed group to emit a respective focused beam directed at the second target location at respective steering angles; (g) applying time delays in accordance with the second set of focal laws to form respective return signals from electrical signals output by the respective group of transducer elements of the second array in response to emission of the focused beams directed at the second target location; (h) selecting a second return signal having a characteristic which indicates it corresponds to an emitted beam that was normal or nearly normal to the part surface at the second target location; and (i) displaying first and second pixels in a column, wherein the first pixel has a value which is a function of at least a parameter value of the first return signal, and the second pixel has a value which is a function of at least a parameter value of the second return signal.

In accordance with yet another aspect, a system for scanning a part is provided comprising: an array of transducer elements; a shoe to hold the array in a position with a steering plane; a pulser/receiver unit capable of sending control signals to and receiving data signals from the array; and a computer system programmed with data acquisition software for controlling the pulser/receiver unit and data analysis software for selecting a respective best signal for each spatial element of the part. The computer system is capable of operating in accordance with the data acquisition software to control the pulser/receiver to perform the following operations: (a) electrically pulsing respective groups of transducer elements of the array in accordance with respective focal laws of a first set of focal laws to emit a plurality of focused beams in sequence, the focused beams being directed at different angles toward a target location on a surface of the part; and (b) after each respective group of transducers is pulsed, receiving electrical signals from the respective group in accordance with respective focal laws of a second set of focal laws to form a respective return signal representing a respective echo returned to a respective group from the inspected part. The computer system is further capable of operating in accordance with the data analysis software to perform the following operations: (c) processing the return signals to derive respective values of a parameter characterizing the return signals; and (d) selecting one of the respective parameter values that satisfies a condition. The system may further comprise a display monitor coupled to the computer system, wherein the computer system is further programmed with software for controlling the display monitor to display a pixel having a value which is a function of at least the selected parameter value.

Other aspects are disclosed and claimed below.

BRIEF DESCRIPTION OF THE DRAWINGS

FIG. 5 is a diagram showing an orthographic view of a portion of a generalized integrally stiffened wing box of an airplane having top and bottom skins or panels connected by a plurality of spars.

FIG. 6 is a diagram showing a side view of a tractor-trailer configuration that includes an active trailer vehicle above and a tractor vehicle below a bottom skin of an integrally stiffened wing box. (A passive trailer vehicle on the other side of the spar is not visible.) The left-hand side of FIG. 6 shows an inspection scenario wherein the trailer vehicles are inverted, while the right-hand side shows an inspection scenario wherein the tractor vehicle is inverted.

FIGS. 16A, 16B and 16C are diagrams showing respective sectional views, the sections being respectively taken along planes indicated by A-A, B-B and C-C in FIG. 16.

DETAILED DESCRIPTION

Figure 1:
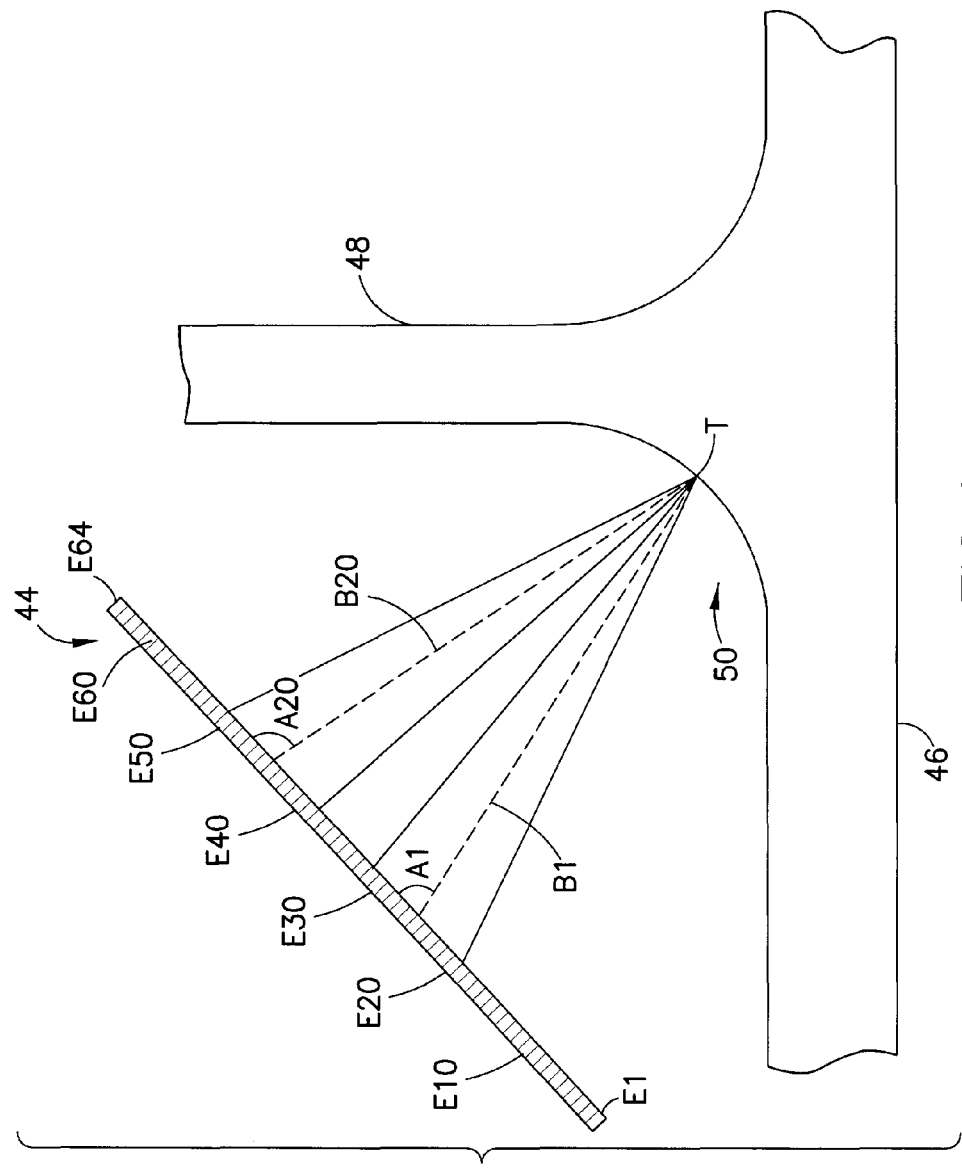
FIG. 1 is a diagram showing two focused and steered beams transmitted at different times from a linear ultrasonic transducer array and toward a part surface of unknown and variable shape.

A process for non-destructive inspection of parts of variable and irregular shape will now be described. The process comprises transmitting sequences of ultrasound beams at a multiplicity of target locations in each of a multiplicity of axially spaced planes and detecting the best return signal for each target location to ensure that the sound enters the part at or nearly at 90 degrees or normal to the confronting surface portion. It is important to keep the direction of ultrasound entry normal to the confronting surface. This process may, for example, be applied in inspection of soft-tooled composite parts, such as wing boxes comprising top and bottom external skins connected by a multiplicity of spars. The filleted join regions (i.e., radii) of such parts, whether they are designed to be constant or to vary by part location, will "vary by manufacturing". This fact creates a difficult and unique mechanical challenge to design and build an apparatus that can maintain sensor-to-part surface normality over a challenging and not-known-in-advance variety of "radial" shapes. In accordance with one implementation, the ability to maintain normality over an unknown "radius" is provided using the data acquisition/analysis techniques and mechanical design described hereinafter.

One embodiment of a system having the ability to scan a part of variable and irregular shape will now be described with reference to a 64-element linear ultrasonic transducer array 44 shown in FIG. 1. For the purpose of illustration, the inspected part is made of composite material and comprises a flange 46, a web 48 and a filleted join region 50, also referred to herein as a "radius" (previously defined).

In accordance with one methodology, a sequence of ultrasonic beams is transmitted in a scan plane at different steering angles, all beams being directed toward the same target location T. Specific orientations of the sequentially transmitted ultrasound beams are achieved electronically by phasing the elements in the array in accordance with stored focal laws. FIG. 1 shows two focused and steered beams B1 and B20 respectively transmitted at the start and end of the aforementioned sequence of transmitted beams. The beams B1 and B20 are shown as being directed to a target location T on the surface of the radius 50.

In the embodiment shown in FIG. 1, the array 44 has 64 ultrasonic transducer elements respectively labeled E1 through E64. However, it should be understood that the non-destructive inspection techniques disclosed herein do not require that the array have 64 elements. The array 44 could have more or fewer elements. Although FIG. 1 shows two beams B1 and B20, it should be understood that beams B1 and B20 are transmitted at different times and are only shown together in FIG. 1 for convenience.

The intent of FIG. 1 is to depict an instance wherein array elements E20 through E31 are sequentially activated in accordance with focal laws designed to produce a focused beam B1 having a steering angle A1. The value of steering angle A1 was selected such that beam B1 would be directed at target location T. (The dashed lines indicate the centerlines of beams B1 and B20.) Such a grouping of sequentially activated elements will be referred to herein as an "aperture". In the example depicted in FIG. 1, the aperture consists of 12 elements. In the case of beam B1, the aperture consists of elements E20 through E31.

FIG. 1 also depicts an instance wherein array elements E39 through E50 are sequentially activated in accordance with focal laws designed to produce a focused beam B20 having a steering angle A20. The value of steering angle A20 was also selected such that beam B20 would be directed at target location T. In the case of beam B20, the aperture consists of elements E39 through E50.

Although not shown in FIG. 1, for the purpose of this discussion it will be assumed that the sequence of transmitted beams directed at target T includes 18 additional beams B2 through B19. In the case of beam B2, the aperture consists of elements E21 through E32; in the case of beam B3, the aperture consists of elements E22 through E33; and so forth. As is well known to persons skilled in the art, for each transmitted beam the same aperture will be employed to detect the echo response and convert that echo response into a respective electrical return signal. As explained in more detail below, for each target location T, the return signals are processed to determine which return signal corresponds to the beam that was closest to being normal to the part surface in the area of target location T (or which return signals correspond to the beams that were closest to being normal).

As is well understood in the art, one set of focal laws are applied when the elements of an aperture are transmitting while another set of focal laws are applied when the same elements transducer the echo response to form a return signal. The focal laws for transmitting and the focal laws for receiving are different yet related by the fact that they are designed to detect, for each transmit beam having a different steering angle, a respective receive beam having the same steering angle. For example, the time delays applied to elements E20 through E31 for detecting a receive beam having a steering angle A1 will be the same as those used to transmit beam B1 having a steering angle A1. The sequence in which echo data is acquired from elements E20-E31 will be the reverse of the sequence in which those same elements were pulsed.

In accordance with the embodiment shown in FIG. 1, the position of array 44 and the focal laws are selected for directing a sequence of beams B1-B20 at target location T with different steering angles with the goal that at least one beam will have a centerline perpendicular or nearly perpendicular to the part surface in the area centered at target location T. For such a ultrasound beam, refraction caused by off angle incidence to the part is minimal. In this instance, the ultrasound beam is said to be normal or nearly normal to the part.

FIG. 1 depicts a situation wherein neither beam B1 nor beam B20 is normal to the part surface at target T. For the purpose of illustration, assume that all beams B1 through B20 have been transmitted and that a beam B8 (not shown in FIG. 1), produced by an aperture consisting of elements E27 through E38, was normal or nearly normal to the part surface at target T. In that event, the amplitude of the return signal generated by transducer elements E27-E38 in response to the echo derived from impingement of beam B8 on the part should have the greatest amplitude of all of the return signals. A pixel value that is a function of that greatest amplitude could then be displayed to indicate the state of the inspected part at the target location T. (Alternatively, a pixel value that is a function of weightings applied to two or more return signal amplitudes meeting certain criteria could be displayed.) This process can be repeated for a multiplicity of targets arranged in rows and columns to produce corresponding rows and columns of pixel values on a display screen (i.e., a computer monitor).

Depending on various factors, the system operator may determine how many beams at different angles should impinge on each target location. Obviously, more beam angles could accommodate more distortion and radius spread for a given application. Adversely, higher beam angle count requires more system throughput in the phased array electronics.

Figure 2:
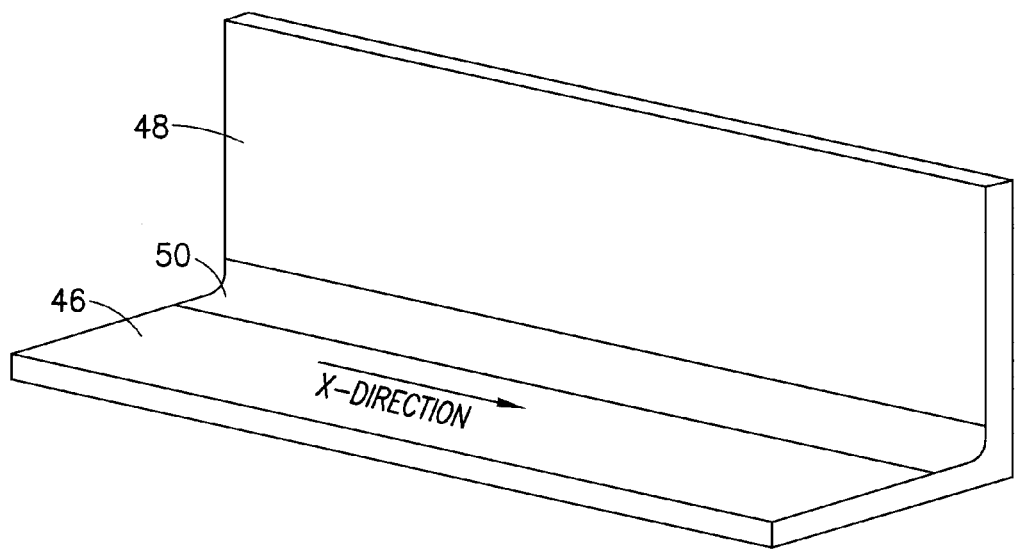
FIG. 2 is a diagram showing an isometric view of a portion of an integrally stiffened wing box with a radius of variable and unknown shape. The arrow indicates a direction of travel of the radius scanner disclosed herein during inspection of the radius, which direction will be referred to herein as the X-direction.

FIG. 2 shows an isometric view of a portion of a composite part to be inspected. Again the inspected part comprises a flange 46, a web 48 (forming an obtuse angle with the flange 46) and a radius 50 (having a variable surface). Using the technique described with reference to FIG. 1, the radius 50 can be scanned in a series of parallel planes separated by equal distances. This is accomplished by moving the ultrasonic transducer array(s) a predetermined incremental distance after each plane has been scanned. The scanner travels along the length of the spar radius in an X-direction indicated by the arrow in FIG. 2. One embodiment of a suitable scanner will be described in detail later with reference to FIGS. 8-16.

The principle of scanning a target location with a multiplicity of ultrasound beams from different angles, detecting the best return signal, and then displaying a pixel value which is a function of that best return signal can be applied in many ways. The number of beams directed at each target location may vary within wide limits. Higher beam counts require greater system throughput in the phased array electronics.

Figure 3:
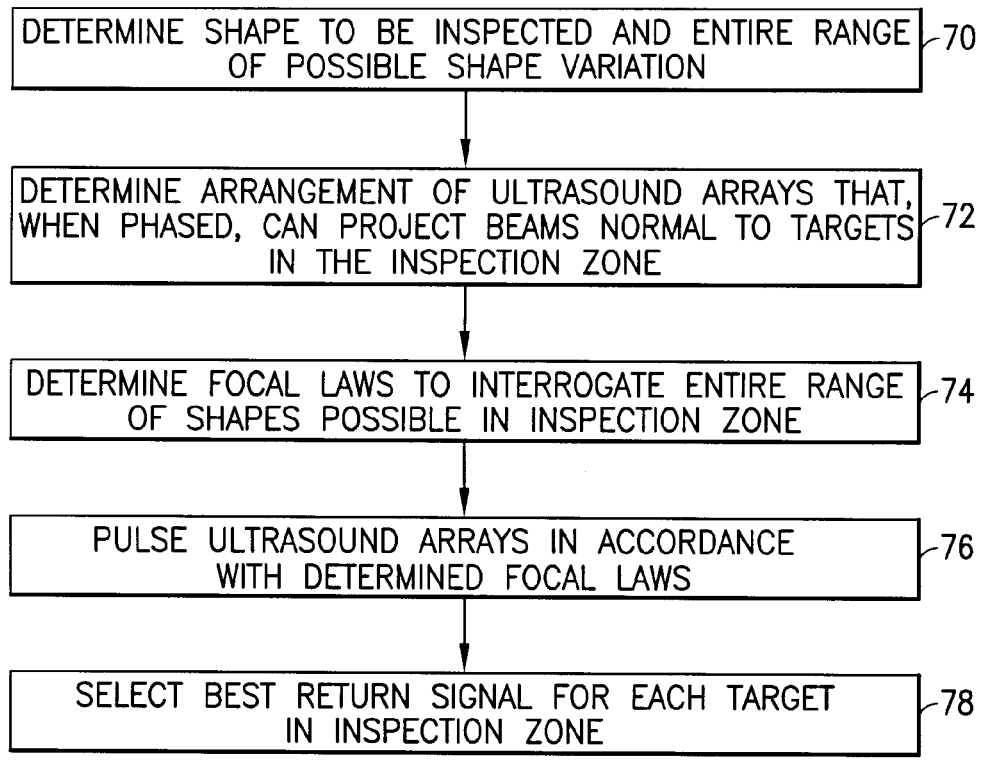
FIG. 3 is a flowchart showing steps of a method for ultrasonic data acquisition in accordance with one embodiment.

FIG. 3 is a flowchart showing steps of a process for designing and implementing a system for inspecting a portion of a part having a surface of unknown shape. The first stage in the process is to determine a shape of an inspection zone and a range of variation thereof (step 70). Then a determination is made how to arrange one or more ultrasonic transducer arrays such that, when phased, these arrays can project ultrasound beams normal to targets to provide complete coverage of the inspection zone (step 72). This includes determining a position (including distance from the inspection zone and orientation relative thereto) of each ultrasonic transducer array such that, when phased, each array can project focused beams at a respective plurality of target locations in the inspection zone (i.e., each array scans a respective separate section of the inspection zone). In step 74 the system designer determines respective sets of focal laws to interrogate the entire range of surfaces possible in the inspection zone. For example, if the surface of the inspected part again has a varying radius between 0.400 (minimum) and 0.600 (maximum) inch, for each array respective sets of targets can be established along an arc length for a 0.500-inch radius midway between the minimum and maximum radius dimensions using a CAD model. For each array, a respective set of focal laws can be determined for the targets along the 0.500-inch radius.

Thereafter, the arrays are placed and oriented in accordance with the array positions that were determined in step 72. During the non-destructive inspection process, the elements of each array would be pulsed in accordance with its respective set of focal laws (step 76) so that the array scans each target with respective focused beams at different steering angles. Then after each respective group of transducer elements has been pulsed to transmit a respective steered beam, the same transducer elements are used to detect returning ultrasound waves from the inspected part and transduce the impinging ultrasound waves into electrical signals, which electrical signals are selected using time delays to form a respective return signal representing a respective received ultrasound beam having a centerline that intersects the target location of the inspected part. For each beam transmitted by the array, the electrical return signals are processed to derive respective values of a parameter characterizing the return signals; then one of the respective parameter values that satisfies a specified condition is selected. In one embodiment, the parameter can be amplitude and the specified condition is which return signal has the greatest amplitude. In another embodiment, one or more other parameter values that satisfy the same or other specified conditions can be selected. In a case where each array projects 20 beams at each target (as was the case shown in FIG. 1), then for each target the "best" return signal or the "best" two or more return signals can be selected from the return signals, wherein the term "best" is used in the sense of satisfying the specified conditions. Later the central computer can process the focal laws corresponding to the selected return signal(s) to determine the vertical position of each target. For each interrogated target location, the parameter value(s) of the best return signal(s) will be processed as a respective pixel value for display on a computer monitor or other display screen at a pixel location corresponding to the target location.

Figure 4:
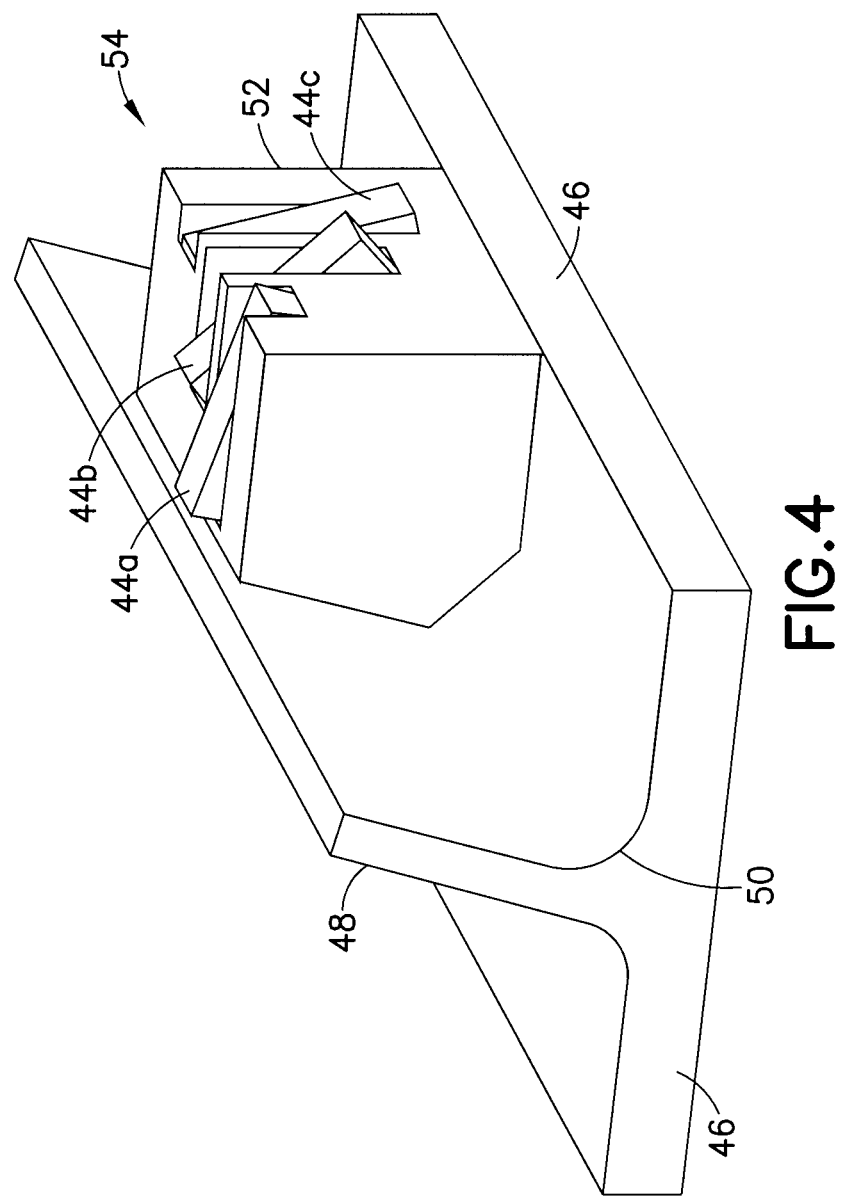
FIG. 4 is a diagram showing an isometric view of a probe having three linear ultrasonic transducer arrays arranged at respective angles in accordance with one embodiment. The carriage and chassis are not shown.

In accordance with one embodiment shown in FIG. 4, three linear ultrasonic transducer arrays 44a, 44b and 44c can be installed in a probe body or shoe 52 and directed with different orientations toward respective portions of a radius 50 having a variable and irregular shape. Each array is responsible for 30 degrees worth of inspection along a 90-degree arc length. In one embodiment, the array 44a is oriented at a 75-degree angle, the array 44b is oriented at a 45-degree angle, and the array 44c is oriented at a 15-degree angle. The shoe and arrays mounted therein form a probe 54 (also referred to herein as a "probe assembly"). As seen in FIG. 4, the probe 54 is located with respect to the flange 46 and the web 48 of the inspected part. The probe 54 is movable along the spar web (in the X-direction indicated in FIG. 2). The probe 54 may be provided with bearings or wheels (not visible in FIG. 4) that contact the flange 46 and web 48, allowing the probe to roll in the X-direction.

Optionally, the probe 54 may be mounted on a chassis (not shown in FIG. 4) that has two sets of magnets, one magnet set for coupling to opposing magnets carried by a tractor vehicle (not shown in FIG. 4) disposed under bottom skin and another magnet set for coupling to opposing magnets carried by a second trailer vehicle (not shown in FIG. 4) disposed on the other side of web 48. The magnets hold the chassis tightly against the flange and web. A system of this type will be described in more detail later with reference to FIGS. 5-7.

The probe 54 is designed to keep the arrays 44a-44c at respective constant distances from the web and flange, allowing the radius dimension to vary underneath the arrays. Since each array is separated by known distances from the web and flange, the aforementioned CAD model is used to measure distances from the array elements to the radius targets and establish beam angles through simple trigonometric functions. In accordance with the implementation described with reference to FIG. 1, apertures consisting of 12 elements are used to create the ultrasound beams at different steering angles. The steering angle for each ultrasound beam can be determined by computing the angle (relative to the linear array) of a line extending from the center point of each aperture to the target. During experimentation, arrays having a pitch of 0.020 inch were used ("pitch" is the separation distance between the centers of adjacent array elements).

In accordance with one implementation, targets are established along an arc length of radius that is midway between the minimum and maximum radius dimensions of a surface of the part to be inspected. For instance, if the surface of the inspected part has a varying radius between 0.400 and 0.600 inch, targets are established along the arc length for a 0.500-inch radius using a CAD model. The distance between the targets at the 0.500-inch radius is selectable by the user but there is a maximum distance established by the nondestructive inspection (NDI) requirements. If, for example, one wanted a target every 5 degrees, for a 90-degree application, there would be 18 targets equally spaced along the arc length.

Focal depth and aperture width (number of elements) are array configuration variables. A person skilled in the art may readily conduct experiments to optimize the configuration data. In one implementation, the array is configured and the pulser/receivers are programmed to produce steered beams having a focal depth of roughly 2 inches. The pulser/receiver may comprise a Tomoscan FOCUS. LT phased array acquisition instrument commercially available from Olympus Corporation. Beams are created by the instrument after defining such variables as element numbers, element spacing, velocity in the water, steering angle, etc. The beams are added into the firing sequence of the instrument and it fires them consecutively after a set distance of probe movement along the length of the composite part (e.g., in the X-direction seen in FIG. 2). The set distance of probe movement serves as the scan resolution and this distance is obtained from an encoder attached to the mobile platform that carries the probe. Currently, because there are 20 different angles for each target T along the radius arc length, it is advantageous to use a respective pulser/receiver for each of the three arrays 44a-44c (see FIG. 4).

In accordance with one implementation, each scan plane is perpendicular to the X-axis and separated from adjacent scan planes by the aforementioned set distance. This spacing determines the horizontal resolution of the pixel image to be displayed. Preferably the resolution is the same in the vertical direction, meaning that the targets will be located along an arc length defined by the intersection of the scan plane and the radius. These targets will preferably be spaced apart by the aforementioned set distance. In one implementation, 21 targets are located along a 90-degree arc length. The 75-degree array 44a is oriented so that it can emit beams toward each of targets Nos. 1-7 in sequence; the 45-degree array is oriented so that it can emit beams toward each of targets Nos. 8-14 in sequence; and the 15-degree array is oriented so that it can emit beams toward each of targets Nos. 15-21 in sequence. It should also be appreciated that arrays 44a-44c are axially displaced relative to each other and can operate concurrently in different scan planes. For example, after array 44a scans targets Nos. 1-7 in the N-th scan plane, the probe will advance axially by the set distance and then array 44a will scan targets Nos. 1-7 in the (N+1)-th scan plane. If the distance separating the arrays 44a-44c is a multiple M times the set distance, then after M incremental advances by the probe, the array 44b will be in position to scan targets Nos. 8-14 in the N-th scan plane. Similarly, after another M incremental advances by the probe, the array 44c will be in position to scan targets Nos. 15-21 in the N-th scan plane.

Table 1 below is an example of a group of beams that can be transmitted from the 45-degree array 44b. A CAD model was used to create this table. Row 8 corresponds to the 8-th target on the radius. The first column labeled "Fire Gp No." in Table 1 is the number of the group of elements (also referred to herein as the "aperture") which are fired to emit a focused steered beam, which group number corresponds to the number of the lowest-numbered element in that group. In the example shown in Table 1, "Fire Gp No. 20" means to fire a group of 12 elements (i.e., aperture width equals 12) starting with element 20 to form a beam. In this example, Fire Gp No. 20 includes elements E20-E31 of a 64-element linear array. As seen in the second column (labeled "Ary Ang") of Table 1, the steering angle of Fire Group No. 20 is −8.8 degrees. The parameter "Part Angle" in the fourth column (labeled "Prt Ang") shows the degree to which the beam having a steered angle of −8.8 degrees is off normal to the inspected part (i.e., the surface area surrounding the 8-th target). The fifth column (labeled "Refr Ang") indicates the angle of refraction of the transmitted beam. Roughly in the middle of this group of beams (i.e., Fire Group No. 30), the part angle and refraction angle are near zero. One should expect the strongest response to come from this beam, provided that the part's radius aligns with the CAD model used to create Table 1.

Table 1 also includes a third column (labeled "Δdb Gain") which shows respective values for a delta decibel gain. Experiments have shown that ultrasonic waves propagating through water (or other acoustic couplant) attenuate with beam angle. The attenuation versus steering beam angle was measured while holding the distance constant. The attenuation is, at least in part, a function of the inefficiency of energy at the higher angles. The propagation distance is assumed to be equal to the length of the beam centerline, which extends from the center of the aperture to the target location. To compensate for the loss due to attenuation, respective values of an instrument gain are introduced for the steering angles. Higher steering angles require more instrument gain.

Table 1 presents data for a group of 20 beams which can be fired at one (i.e., the 8-th) target from different directions. In accordance with one implementation, the 45-degree array transmits respective groups of beams directed at 7 (i.e., the 8-th through 14-th) targets, resulting in 140 beams. In other implementations, the targets can be closer together, resulting in more than 7 targets located along a 30-degree arc length. Also, in accordance with other implementations, the number of steered beams directed toward each target location can be more or less than 20.

TABLE 1

Row 8

| Fire Gp No. | Ary Ang | Δdb Gain | Prt Ang | Refr Ang |
|---|---|---|---|---|
| 20 | −8.8 | 1.11 | 12.5 | 27.9 |
| 21 | −10.2 | 1.55 | 11.1 | 24.8 |
| 22 | −11.5 | 2.03 | 9.8 | 21.7 |
| 23 | −12.8 | 2.50 | 8.5 | 18.8 |
| 24 | −14.1 | 3.00 | 7.2 | 15.8 |
| 25 | −15.3 | 3.68 | 6.0 | 13.0 |
| 26 | −16.6 | 4.41 | 4.7 | 10.2 |
| 27 | −17.9 | 5.13 | 3.4 | 7.5 |
| 28 | −19.1 | 5.77 | 2.2 | 4.8 |
| 29 | −20.3 | 6.40 | 1.0 | 2.2 |
| 30 | −21.5 | 7.04 | −0.2 | −0.4 |
| 31 | −22.7 | 7.73 | −1.4 | −2.9 |
| 32 | −23.8 | 8.40 | −2.5 | −5.5 |
| 33 | −24.9 | 9.01 | −3.6 | −7.9 |
| 34 | −26.1 | 9.67 | −4.8 | −10.4 |
| 35 | −27.1 | 10.38 | −5.8 | −12.8 |
| 36 | −28.2 | 11.21 | −6.9 | −15.2 |
| 37 | −29.3 | 12.28 | −8.0 | −17.5 |
| 38 | −30.3 | 13.32 | −9.0 | −19.8 |
| 39 | −31.3 | 14.50 | −10.0 | −22.1 |

In accordance with one application, the method described above can be used in the non-destructive inspection of an integrally stiffened wing box of an aircraft e.g., a horizontal stabilizer made of composite material. A portion of a generalized integrally stiffened wing box 2 is depicted in FIG. 5. The depicted integrally stiffened wing box comprises a top skin 4 and a bottom skin 6 connected by a plurality of internal vertical support elements, hereinafter referred to as "spars". Each spar comprises a web 8 and respective pairs of filleted join regions 10 (also called "spar radii" herein), which connect the spar web 8 to the top and bottom skins. As used herein, the terms "top skin" and "bottom skin" refer to the relative positions of two skins of a wing box during inspection, not when the wing box is installed on an airplane (i.e., a wing box may be inverted for inspection).

In accordance with one embodiment, a probe (comprising a shoe and one or more linear ultrasonic transducer arrays) is transported down the length of a tunnel through the interior of a hollow composite structure. For this type of inspection, the probe is carried by a trailer vehicle (not shown in FIG. 5) placed inside the hollow structure 2. This trailer vehicle can be characterized as being "active" in the sense that equipment it carries is actively performing a scanning function. Each array needs to be acoustically coupled to each surface being inspected. This is accomplished by providing a column of water that flows between the array and the inspected part. An automated tractor vehicle (also not shown in FIG. 5) moves the active trailer vehicle along the spar web 8.

In FIG. 5, portions of the interior surfaces of the part which need to be inspected can be seen. Each spar may need to have all four filleted join regions 10 and each web 8 inspected. This is a challenging inspection as each cavity is essentially a long rectangular tunnel that may increase or decrease in cross section as one moves from one end to the other. The top and bottom skins 4 and 6 can be inspected from the exterior using conventional NDI techniques which are not part of this disclosure In accordance with one embodiment for inspecting structures of the type shown in FIG. 5, an external motorized and computer-controlled tractor is magnetically coupled to an internal active trailer that holds and positions one or more ultrasonic transducer arrays on the interior of the part. Also, there is an internal passive trailer on the opposite side of the spar that is magnetically coupled through the spar to the active trailer and also magnetically coupled through the skin to the tractor. This three-part system gives a very stable system for positioning and moving the ultrasonic transducers. One embodiment of such a three-part system will now be described with reference to FIGS. 6 and 7.

Figure 7:
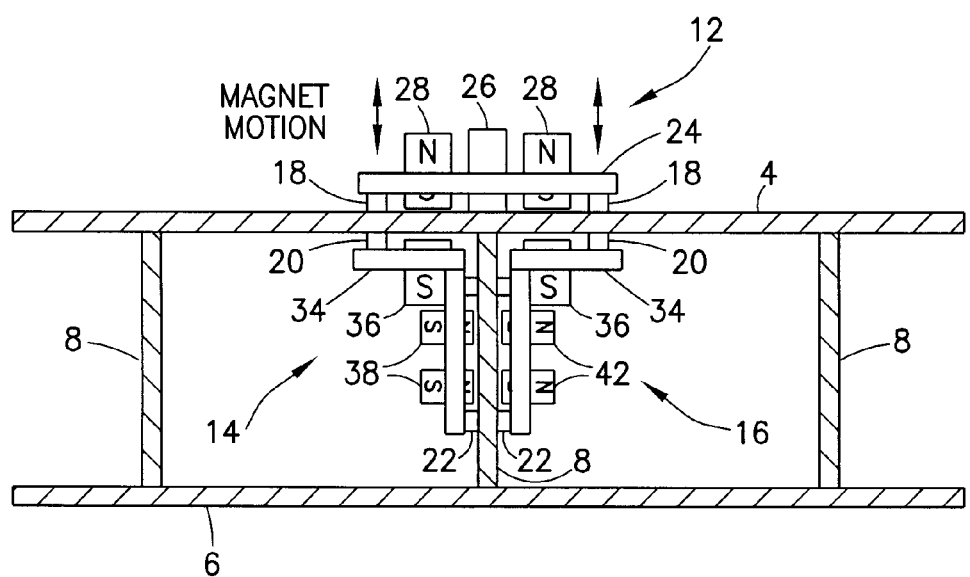
FIG. 7 is a diagram showing an end view of the tractor-trailer configuration depicted on the left-hand side of FIG. 6 (with respective inverted trailer vehicles disposed on both sides of a spar).

FIG. 6 shows side views of a tractor-trailer configuration in accordance with one embodiment in two different inspection situations (motor actuators are not shown). The automated NDI inspection system comprises a traction-motor powered tractor vehicle 12, which rides on the external surface of top skin 4 or bottom skin 6 of integrally stiffened wing box 2, and a pair of trailer vehicles (only trailer vehicle 14 is visible in FIG. 6, the other being hidden behind a spar web 8), which ride along an internal surface of the top or bottom skin. The left-hand side of FIG. 6 shows an inspection scenario wherein the tractor vehicle 12 is outside the integrally stiffened wing box in a non-inverted position while the trailer vehicles are inside the integrally stiffened wing box in inverted positions; the right-hand side of FIG. 6 shows an inspection scenario wherein the tractor vehicle 12 is outside the integrally stiffened wing box in an inverted position while the trailer vehicles are inside the integrally stiffened wing box in non-inverted positions. FIG. 7 shows an end view of the tractor-trailer configuration depicted on the left-hand side of FIG. 6, with inverted trailer vehicles 14 and 16 disposed on opposite sides of the spar web.

In the inspection scenario depicted in FIG. 7 (and the left-hand side of FIG. 6), idler wheels 18 of tractor vehicle 12 contact and roll on the external surface of top skin 4 while vertical idler wheels 20 of inverted trailer vehicles 14 and 16 (only one such idler wheel is visible in FIG. 7 for each trailer vehicle) contact and roll on the internal surface of top skin 4, and the horizontal idler wheels 22 roll on the spar web surface. The right-hand side of FIG. 6 shows an alternative situation wherein idler wheels 18 of the inverted tractor vehicle 12 contact and roll on the external surface of bottom skin 6 while vertical idler wheels 20 of trailer vehicle 14 (and also idler wheels of trailer vehicle 16 not visible in FIG. 6) contact and roll on the internal surface of bottom skin 6, and the horizontal idler wheels 22 roll on the spar web surface.

In accordance with the embodiment partly depicted in FIGS. 6 and 7, the tractor vehicle 12 comprises a frame 24. Four idler wheels 18 (only two of which are visible in each of FIGS. 6 and 7) are rotatably mounted to frame 24 in a conventional manner. (Alternative embodiments may include more idler wheels.) The idler wheels 18 are made of plastic and have smooth contact surfaces. Tractor vehicle motion is enabled by driving a drive wheel 26 (also rotatably mounted to frame 24) to rotate. Drive wheel 26 is coupled to a motor 30 via a transmission (not shown). The drive wheel 26 is positioned on the frame 24 so that it is in frictional contact with skin 4 or 6 when idler wheels 18 are in contact with the same skin. The drive wheel is made of synthetic rubber material. The surface of the drive wheel may have a tread pattern. In addition, the tractor vehicle 12 carries multiple permanent magnets 28. Each permanent magnet 28 has North and South poles, respectively indicated by letters "N" and "S" in the drawings.

Still referring to FIGS. 6 and 7, each trailer vehicle 14, 16 is comprised of a frame 34. For each trailer vehicle, two vertical idler wheels 20 (only one of which is visible in FIG. 7) and four horizontal idler wheels 22 (only two of which are visible in FIG. 7) are rotatably mounted to frame 34 in a conventional manner. (Alternative embodiments may include more idler wheels.) Each trailer vehicle 14, 16 carries multiple vertically mounted permanent magnets 36, the North poles of which are magnetically coupled to the South poles of confronting permanent magnets 28 carried by the tractor vehicle 12. In the design described by FIGS. 6 and 7, each trailer has two vertically mounted permanent magnets 36, but other designs may use different configurations. The positions and pole orientations of the magnets may have other configurations as long as the N-S pairing and relative alignment of the magnets between the tractor and trailer are preserved.

As seen in FIG. 7, in addition to being magnetically coupled to the tractor vehicle 12, the trailer vehicles 14 and 16 are magnetically coupled to each other using additional sets of permanent magnets 38 and 42. As seen in FIG. 6, trailer vehicle 14 carries four horizontally mounted permanent magnets 38. Trailer vehicle 16 also carries four horizontally mounted permanent magnets 42 (only two of which are visible in FIG. 7), the poles of which are respectively magnetically coupled to opposing poles of the permanent magnets 38 on trailer vehicle 14. This magnetic coupling produces an attraction force that holds idler wheels 22 of trailer vehicles 14 and 16 in contact with opposing surfaces of an intervening spar.

As seen in FIG. 6, trailer vehicle 14 further carries a payload 40. For the NDI scenario depicted in FIGS. 6 and 7, payload 40 is a probe assembly comprising a shoe with three linear ultrasonic transducer arrays disposed at three different angles. As previously noted, the arrays must be acoustically coupled to the surface being inspected. For example, the inspected region is covered with a constant stream of water to acoustically couple the ultrasonic sensor to a filleted join region 10. Magnetically coupled systems are well suited for operation with water in the environment.

As the tractor vehicle is driven to travel along a desired path on the outer surface of the top or bottom skin, it pulls the inner trailer vehicles along. The magnetic coupling system described above keeps the inverted vehicle(s) in contact with the surface it rides on. For wing box applications, two magnetically coupled trailer vehicles can be used, one on each side of the spar, as shown in FIG. 7. This allows the system to take advantage of the internal structure of the scanned object as a guide to allow the system to track properly along the surface.

The system partly depicted in FIGS. 6 and 7 further comprises means (not shown) for automatically adapting to the variable thickness of the intervening skin or panel (i.e., top skin 4 or bottom skin 6) by raising or lowering the magnets (which magnet motion is indicated by double-headed arrows in FIG. 6) on the tractor vehicle as it moves along the structure being inspected. Further details concerning the trailer-tractor configuration depicted in FIGS. 6 and 7 (and alternative embodiments) are disclosed in U.S. patent application Ser. No. 13/313,267, the disclosure of which is incorporated by reference herein in its entirety.

An apparatus for inspecting filleted join regions 10 (hereinafter "radii") of an elongated and tapered hollow structure will now be described. The active trailer vehicle for scanning a spar radius will be referred to herein as a "radius scanner". In the embodiment shown in FIG. 7, the trailer vehicle 14 is designed to work with the tractor on the top or bottom of the integrally stiffened wing box (or other composite structure having cavities between webs). The radius scanner 14 carries a probe that operates as previously described under the control of a computer that host data acquisition/analysis software. The radius scanner may also have a video camera (not shown) that captures a live view of the probe.

The X-axis motion (the X axis being parallel to the spar radius being inspected if the spar radius is linear) is provided by the tractor vehicle of the system, which uses data from a rotational encoder attached to an idler wheel on the trailer vehicle. The trailer component is pulled by the tractor and carries the probe assembly. The X-motion drive motor can be a programmable stepper motor that can communicate with the computer through a serial communications interface. The operator or automated path planning system specifies the desired incremental movements, direction, and an optional final goal position of the tractor-trailer system through a motion control software application. The X-axis positioning is controlled using proportional feedback of the encoder count data.

One implementation of a radius scanner equipped with a scanning system that employs linear phased arrays in the manner described above will now be described with reference to FIGS. 8-16. This implementation differs from the embodiment depicted in FIG. 4 in the respect that the three arrays are not held in fixed positions by a single probe body. Instead the 15-degree and 45-degree arrays are fixed in respective cavities of a web rider body, while the 75-degree array is carried by a flange rider that can pivot relative to the web rider body. This arrangement will be described in detail below.

Figure 8:
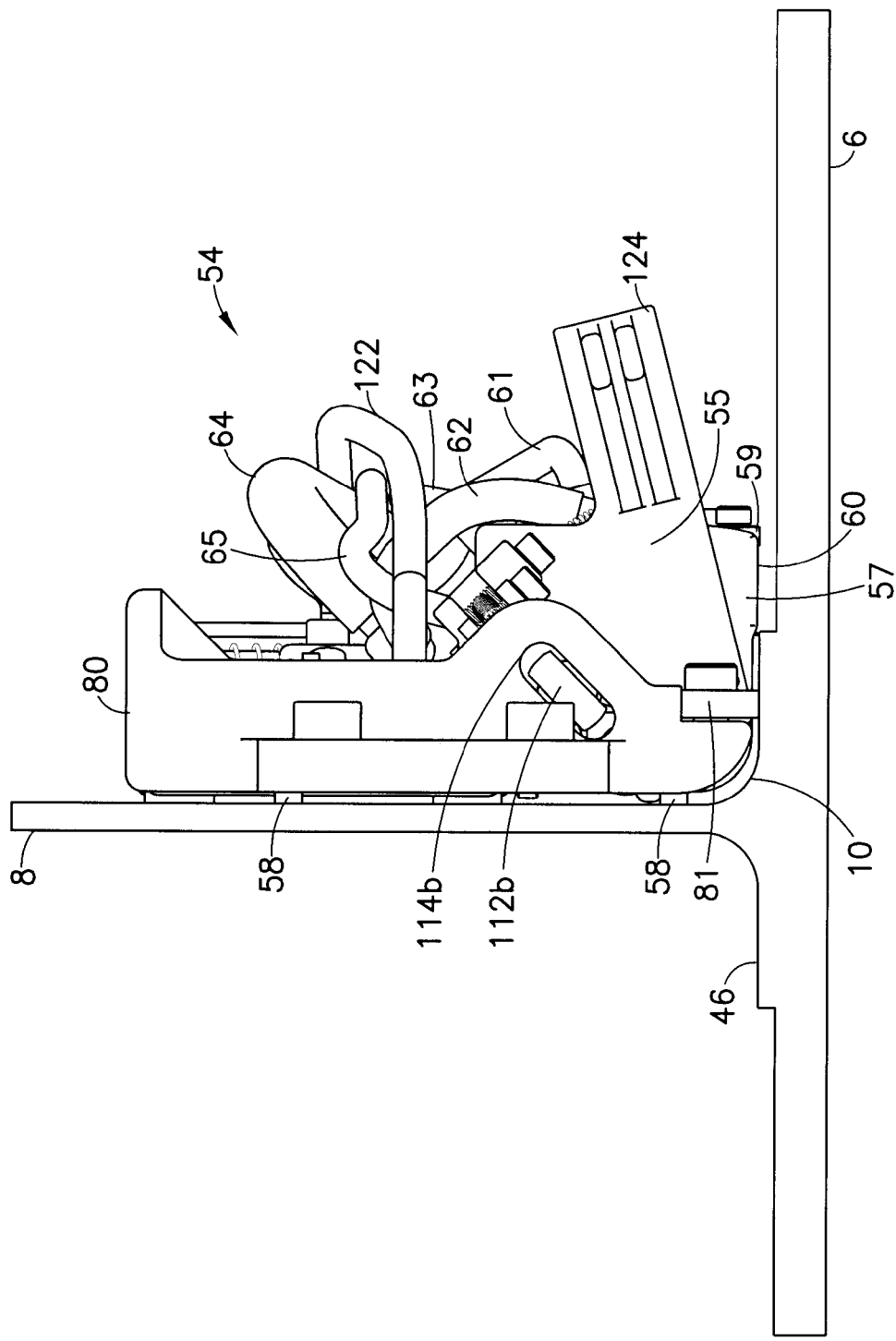
FIG. 8 is a diagram showing an end view of a probe in accordance with an alternative embodiment. The probe is shown in its normal operating position. (The near-side magnet pods of the radius scanner are not shown for clarity.)

FIG. 8 shows an end view of a radius scanner with its probe 54 in its normal operating position relative to portions of a wing box, including a bottom skin 6, a spar web 8, and a radius 10. (The near-side magnet pods of the radius scanner are not shown in FIG. 8 for clarity). The thicker portions of bottom skin 6 adjacent spar web 8 are referred to herein as flanges 46. The radius scanner comprises a carriage frame 80 that supports the probe assembly 54 by means of links (including a socket link 112*b* disposed in a slot 114*b* seen in FIG. 8, but described in detail later with reference to FIG. 12).

The probe assembly 54 comprises a web rider body 55 that supports the 15- and 45-degree arrays in fixed positions and further supports a pivotable flange rider 57 that holds the 75-degree array. The flange rider 57 is pivoted so that the 75-degree array will always be parallel to the flange surface as the manufactured angle between web and flange varies along the length of the part. The web rider body 55 has a set of four web rider wheels 58 (only two of which are visible in the FIG. 8) which contact the web 8. The carriage frame 80 has a pair of wheels 81 (only one of which is visible in FIG. 8) which contact the flange 46. FIG. 8 also shows a single flange rider wheel 59, which is shown in more detail in FIGS. 13 and 16A (described later). Wheel 59 is rotatably mounted on the flange rider 57. As depicted in FIG. 8, the flange rider wheel 59 does not always contact the part, depending on which portion of the part is being inspected. The flange rider 57 has a pair of rubbing ridges 60 which are provided for places where the flange 46 does not extend out to the flange rider wheel 59.

Figure 9:
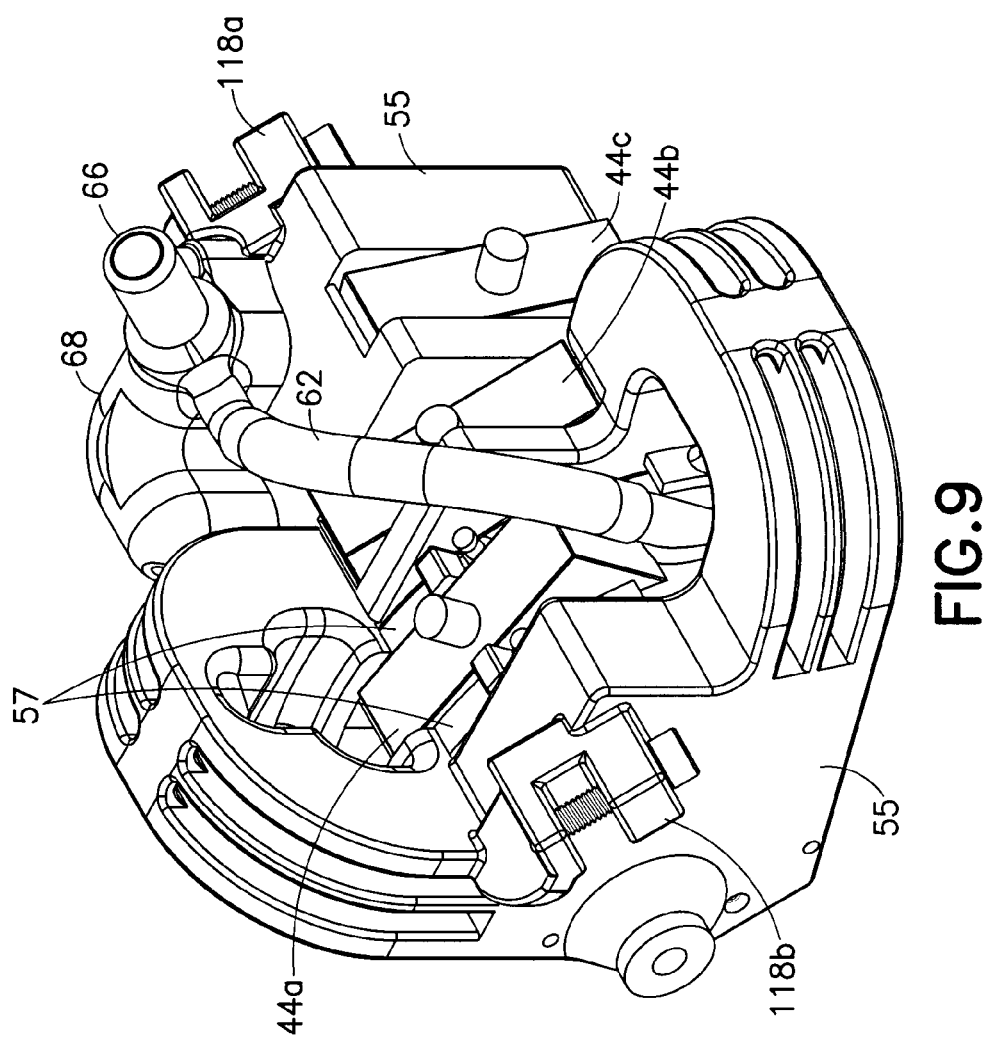
FIG. 9 is a diagram showing an isometric view of the probe assembly depicted in FIG. 8, but with electrical cabling omitted.

FIG. 9 shows an isometric view of a probe assembly in accordance with one embodiment in which the ultrasonic arrays are held by a web rider body 55 and a flange rider 57 pivotably mounted in a cavity in the web rider body 55. This probe assembly is incorporated in the probe/carriage assembly depicted in FIG. 12. (However, other probe assemblies can be used with the probe/carriage assembly depicted in FIG. 12.) The 45-degree array 44*b* and 15-degree array 44*c* are fixed inside respective cavities formed in the web rider body 55. The 75-degree array 44*a* is carried by the pivotable flange rider 57.

FIG. 8 also shows the signal cabling for the ultrasonic transducer arrays, including cable 61 which is connected to the 15-degree array, cable 63 which is connected to the 45-degree array, and cable 65 which is connected to the 75-degree array. Cable 122 is connected to the X-position encoder (described with reference to FIG. 11 below). The electrical cabling has been omitted from FIG. 9 to allow a clear view of the ultrasonic transducer arrays 44*a*-44*c*.

Ultrasonic inspection at the frequency used by the system disclosed herein requires the presence of an acoustic couplant between each ultrasonic transducer array and the inspected part. The scanning system shown in FIG. 8 uses water as the acoustic couplant. The probe 54 has three water cavities (not shown in FIG. 8, but see items 110*a*-*c* in FIGS. 16A-C respectively)) which are supplied with water via a water supply tube 64 that is connected to an inlet of a water manifold (not shown in FIG. 8). FIG. 9 shows the inlet 66 of water manifold 68. Water is supplied from the manifold 68 to the water cavity for array 44*a* by means of a tube 62. Water is supplied to the water cavities for arrays 44*b* and 44*c* by means of the water manifold 68. More details will be provided later when FIGS. 16A-16C are described.

In accordance with one implementation, the carriage frame 80 is part of a chassis that is magnetically coupled to a tractor vehicle and to a passive trailer vehicle, as previously described with reference to FIGS. 6 and 7. The chassis and probe assembly form an active trailer vehicle that will hereinafter be referred to as a "radius scanner". The chassis will described in detail with reference to FIGS. 10 and 11.

Figure 10:
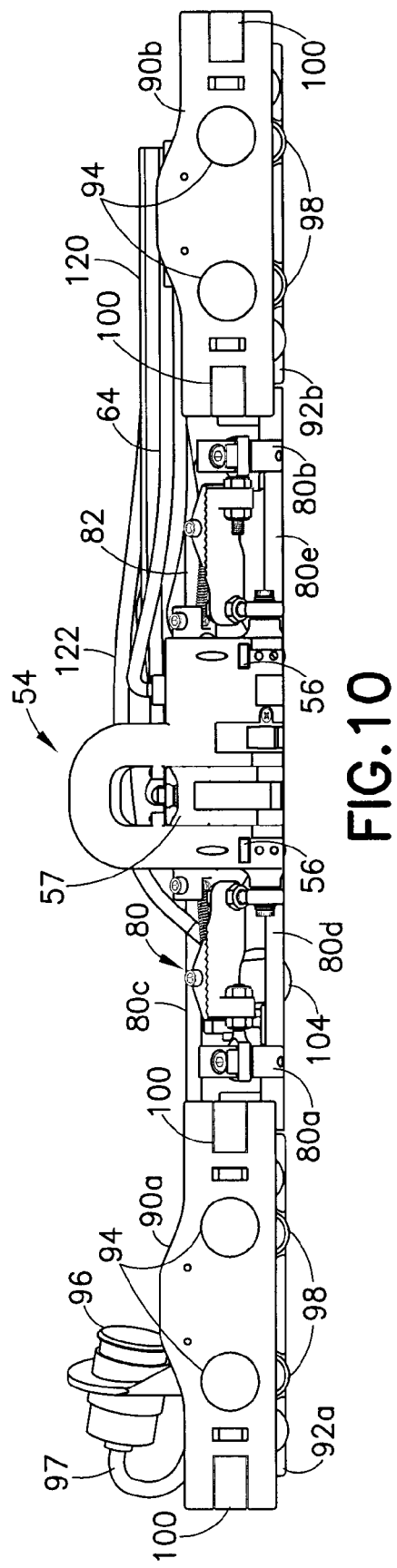
FIGS. 10 and 11 are diagrams showing back and bottom views of a radius scanner in accordance with one implementation.
Figure 11:
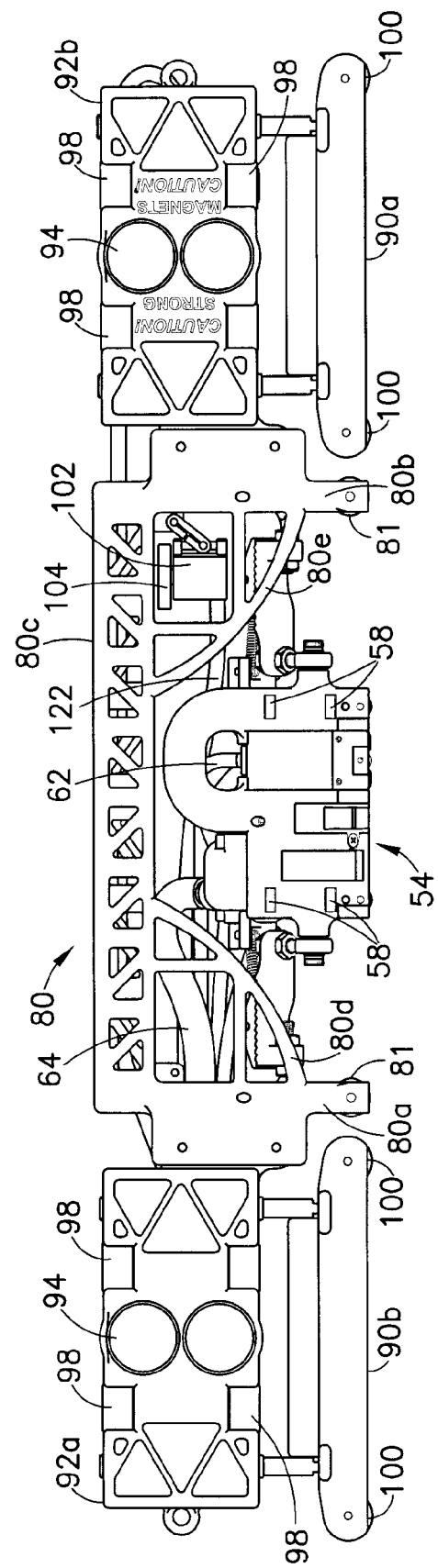

FIGS. 10 and 11 show back and bottom views of a radius scanner in accordance with one implementation. As best seen in FIGS. 10 and 11, this radius scanner comprises a rigid carriage frame 80 having two side members 80*a* and 80*b*, a back 80*c* which connects the rear end of the side members 80*a*-*b*, and ribs 80*d* and 80*e* which connect to back 80*c* and to the respective side members 80*a*-*b*.

The radius scanner shown in FIGS. 10 and 11 will be magnetically coupled to a tractor vehicle on the other side of a flange by means of two through-flange magnet trolleys 90*a*, 90*b* and magnetically coupled to a passive trailer vehicle on the other side of a web by means of two through-web magnet trolleys 92*a*, 92*b*. Each magnet trolley carries a pair of magnets 94 for magnetic coupling to magnets of opposite polarity carried by the tractor vehicle and other trailer vehicle, as previously described. Each through-web magnet trolley has four wheels 98, which contact a web surface. Each through-flange magnet trolley has two wheels 100, which contact a flange surface. As best seen in FIG. 11, each through-flange magnet trolley 90*a*, 90*b* is adjustably mounted to a corresponding through-web magnet trolley 92*a*, 92*b*. The latter, in turn, are respectively rigidly connected to respective side members 80*a*, 80*b* of the carriage frame 80. A video camera 96 (with scene illumination lamps) is mounted on through-web magnet trolley 92*b* (see FIG. 10). The video camera 96 monitors operations, sending video images back to the central computer via a cable 97.

Referring to FIG. 11, the X-position of the probe 54 is measured by an X-direction encoder 102, which encodes rotation of an encoder wheel 104 mounted to the carriage frame 80. The encoder wheel 104 rides on the web surface as the radius scanner travels along a radius. The encoder wheel 104 is shown in FIG. 10 in its extended position, which occurs when the radius scanner is separated from the web surface (i.e., no longer in contact). The encoder 102 sends an encoder pulse to the operations control center (via encoder cable 122) after each incremental movement of the scanner in the X-direction, which encoder pulses are used by a control computer and by ultrasonic pulser/receiver devices to determine the X-coordinate of each scan plane in a well-known manner.

The water supply tube 64, the signal cabling (items 61, 63 and 65 in FIG. 8) for the ultrasonic transducer arrays, the camera cable 97 and the encoder cable 122 all pass through a supply umbilical 120 (see FIG. 10) which connects the radius scanner to the operations control center. The water supply tube 64 is connected in this way to a water supply (not shown in the drawings) The signal cabling for the ultrasonic arrays is connected the pulser/receiver devices (not shown in FIGS. 10 and 11). Video from the camera is received by a display monitor (item 134 in FIG. 17) via a camera switch (not shown in the drawings). The encoder pulses are ultimately received by the ultrasonic pulser/receiver devices and the control computer (items 82 and 84 in FIG. 17), as previously described.

Figure 12:
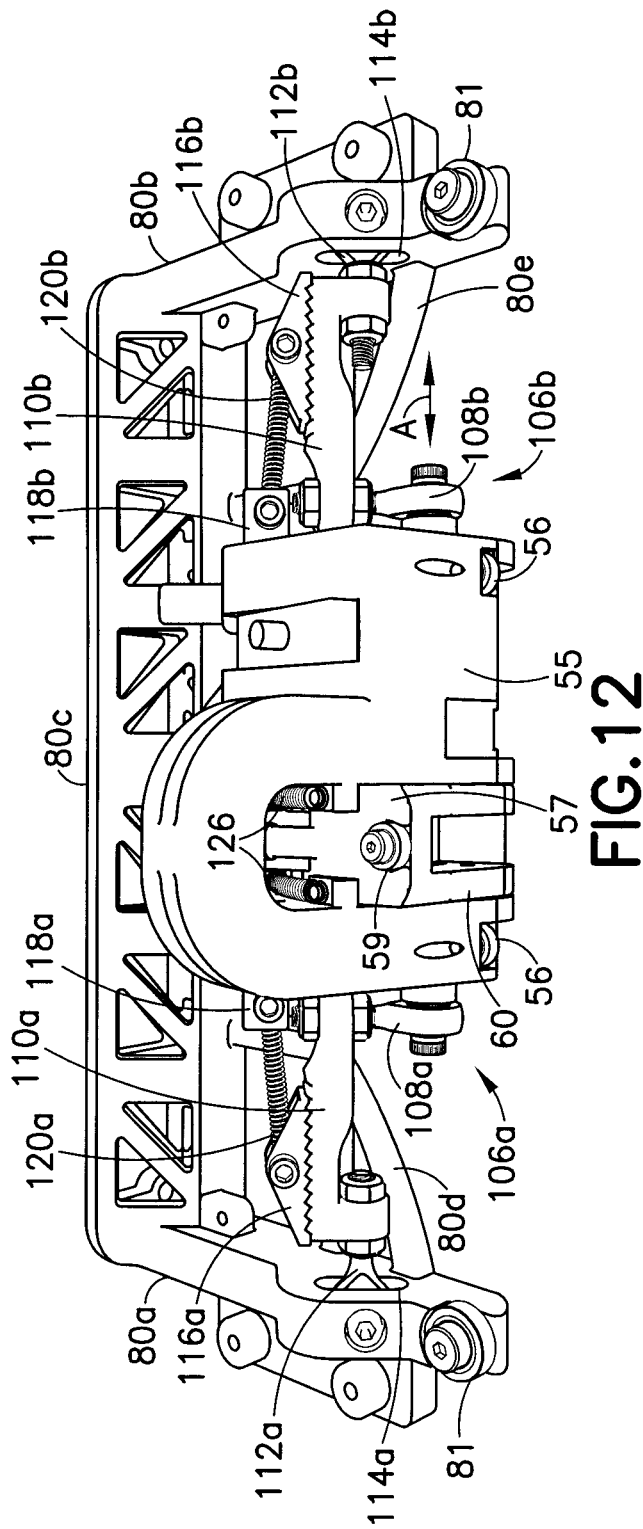
FIG. 12 is a diagram showing an isometric view of a probe/carriage assembly incorporated in the radius scanner depicted in FIGS. 10 and 11.

FIG. 12 shows an isometric view of a probe/carriage assembly incorporated in the radius scanner depicted in FIGS. 10 and 11. The probe/carriage assembly comprises a web rider body 55 supported by a flex carriage. The flex carriage comprises carriage frame 80 and a set of linkages which bias the web rider body 55 against the radius at roughly an angle that bisects the angle between the web and the flange surfaces. This allows the probe assembly to passively adjust its position while held in contact with internal surfaces of the spar web and adjacent skin In this implementation, the flex carriage supports the web rider body 55 in a manner that allows the latter to travel toward/away from a radius by a total travel distance of less than ¼ inch during normal operation. A person skilled in the art will recognize that a flex carriage could be designed to achieve any desired total travel distance. Because the carriage frame 80 can move sideways on the web into the flange, the web rider body 55 also has a pair of web rider flange-stop wheels 56 which stop the web rider body from contacting the flange. A pair of compression springs 126 push the pivotable flange rider 57 into the flange (not shown).

Still referring to FIG. 12, the flex carriage is coupled to the probe assembly 54 by means of a pair of ball-and-socket joints 106a and 106b. Each ball-and-socket joint comprises a respective socket link 108a/108b (hereinafter "first and second socket links"), which are parts of the flex carriage, and a respective ball link (hereinafter "first and second ball links"), which are parts of the probe assembly. The flex carriage further comprises a pair of arms 110a and 110b. The first socket link 108a is fastened to one end of arm 110a; the second socket link 108b is fastened to one end of arm 110b. In addition, each side member 80a,b has a respective slot 114a,b in which third and fourth socket links are respectively coupled to third and fourth ball links (not visible in FIG. 12) to form third and fourth ball-and-socket joints. The only components of the third and fourth ball-and-socket joints visible in FIG. 12 are the third and fourth socket links 112a,b. The slots 114a,b are both disposed at an angle roughly equal to 45 degrees and have a slot width which limits the angular travel of socket links 112a,b from a pressure plane. The first and second socket links 108a and 108b are oriented to limit angular travel off normal to the pressure plane. Slight motion in the directions indicated by the double-headed arrow A in FIG. 12 is taken up by the tolerances in the ball-and-socket joints.

The flex carriage shown in FIG. 12 further comprises a pair of flex spring arm anchors 116a and 116b which can be attached to arms 110a and 110b respectively, the positions of the former relative to the latter being adjustable. The probe 54 further comprises a pair of flex spring probe anchors 118a and 118b. The opposing arm and probe anchors are coupled by means of respective flex springs 120a and 120b. One end of flex spring 120a is hooked onto arm anchor 116a and the other end is hooked onto probe anchor 118a; one end of flex spring 120b is hooked onto arm anchor 116b and the other end is hooked onto probe anchor 118b. These springs provide a biasing force. The net force is into the web/flange joint, leaving enough freedom of motion to allow the probe body to follow the uneven surface on its own contact wheels.

The implementation depicted in FIGS. 10-12 is only one way of pressing the probe body into the radius. The same functionality could be achieved using apparatus of different designs.

In accordance with an alternative embodiment, the probe assembly could be driven (e.g., by a stepper motor) to pivot about an axis that is parallel to the X-direction. In that case, an array could transmit one group of beams toward an N-th target while the probe assembly is stationary; then the probe assembly would be rotated about its pivot axis by a specified number of degrees (e.g., 5 degrees); then the array could transmit another group of beams toward an (N+1)-th target while the probe assembly is again stationary; and so forth.

Figure 13:
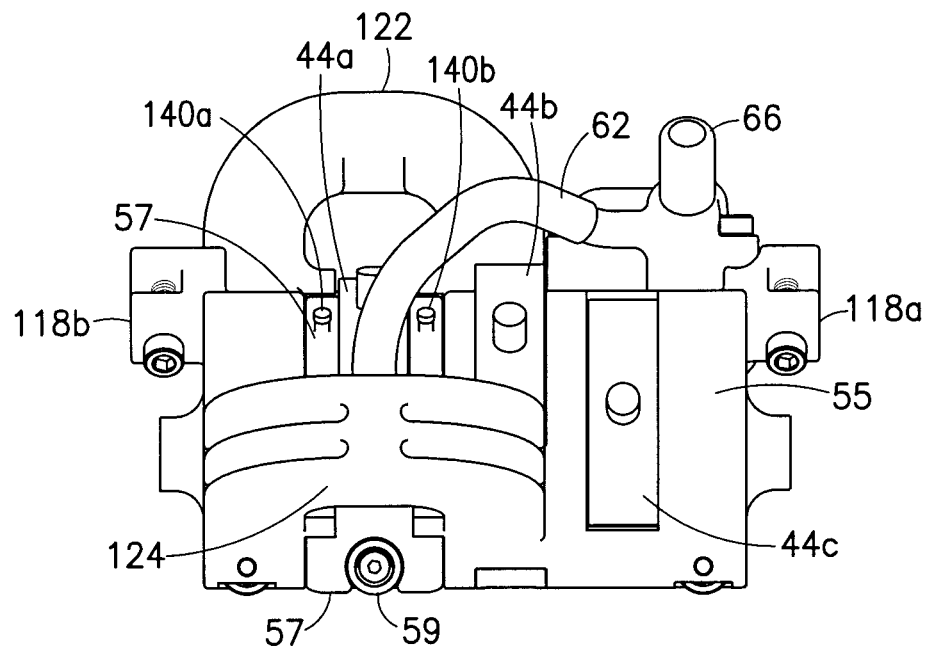
FIGS. 13 through 16 are diagrams which respectively show front, side, bottom and top views of the probe assembly depicted in FIGS. 8 and 9.
Figure 14:
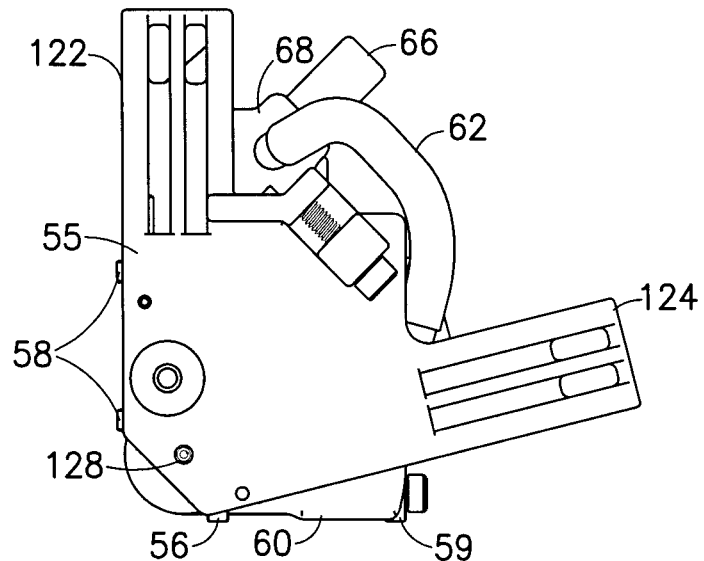
Figure 15:
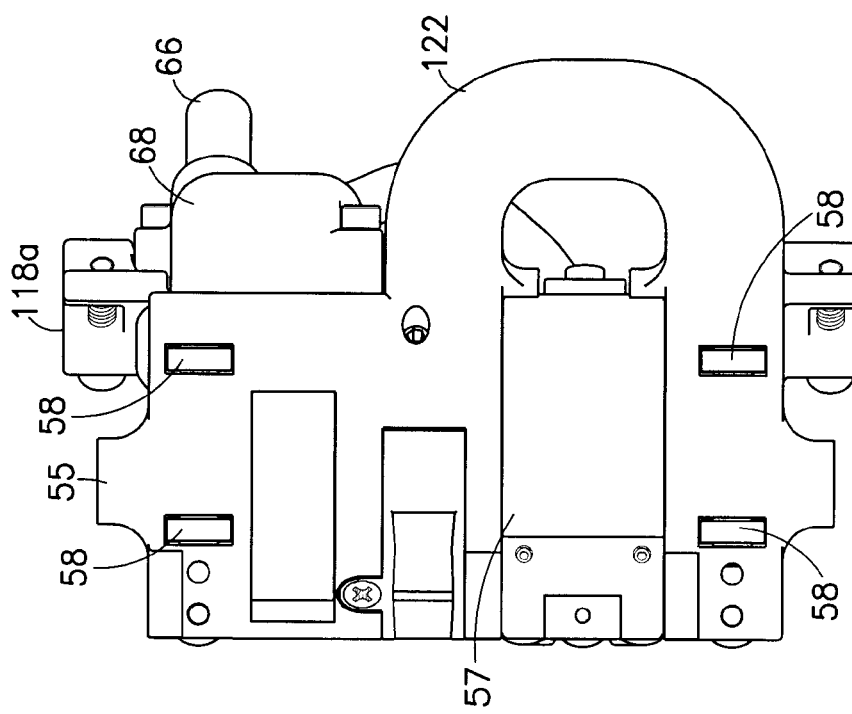

FIGS. 13 through 16 show front, side, bottom and top views of the probe assembly depicted in FIG. 9. FIG. 13 shows a pair of flange rider spring posts 140a,b. Respective ends of compression springs 126 shown in FIG. 12 are hooked onto flange rider spring posts 140a,b, enabling these springs to bias the flange rider to pivot in a direction toward the flange. FIG. 14 shows the flange rider pivot axis 128. The probe assembly comprises a pair of strongbacks 122 and 124 which mechanically stabilize the far end of the flange rider pivot axis. FIG. 15 shows the probe assembly 54 seen in FIG. 11, but on a magnified scale.

Figure 16:
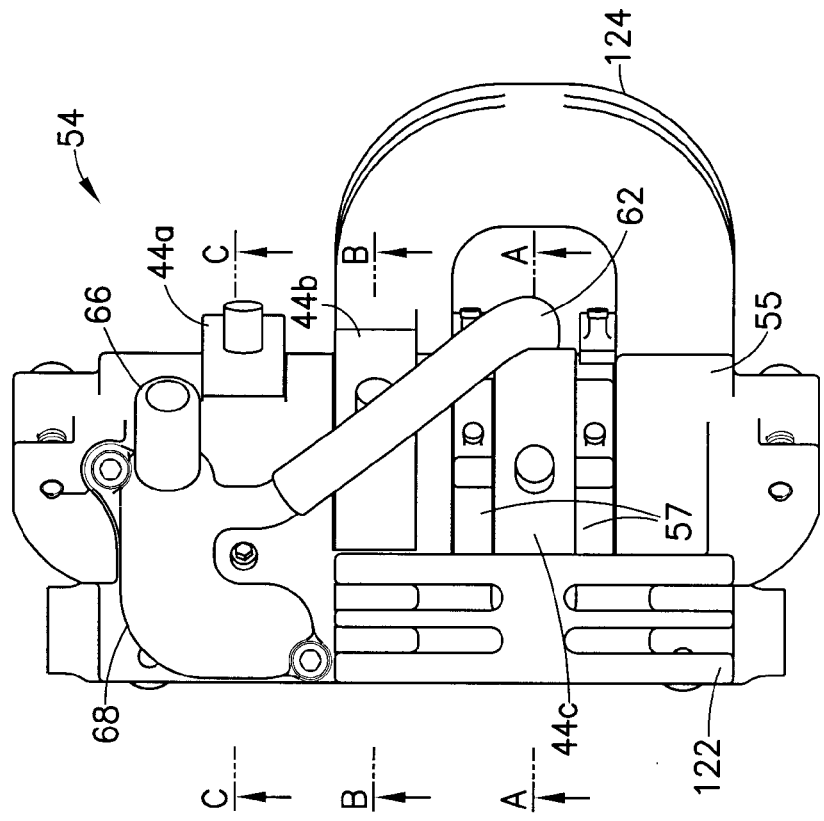

FIGS. 16A, 16B and 16C are diagrams showing respective sectional views, the sections being respectively taken along planes indicated by A-A, B-B and C-C in FIG. 16. Section A-A passes through the 75-degree array 44c; section B-B passes through the 45-degree array 44b; and section C-C passes through the 15-degree array 44a.

The section plane for FIG. 16A also passes through the flange rider wheel 59, which comprises the outer race of a roller bearing whose inner race is held in a fixed position by a screw 132. The flange rider wheel 59 rides on the flange (where the flange is wide enough to engage it). In some places the part flange is a bit narrower, and the flange rider slides along on plastic rubbing ridges 60. The function of both of these is to hold the flange rider at a constant distance from the planar surface of the flange.

As seen in FIG. 16A, the flange rider 57 comprises a passageway 30 which is in fluid communication with tube 62. Water supplied via tube 62 flows through passageway 130 and another internal passageway (not shown), and then enters the water cavity 110a via a water inlet 112a. Referring to FIGS. 16B and 16C, water from the water manifold 68 flows onto water cavities 110b and 110c via respective water inlets 112b and 112c. The supply of water should be sufficient to continuously fill all of the water cavities 110a-c during scanning operations.

Figure 17:
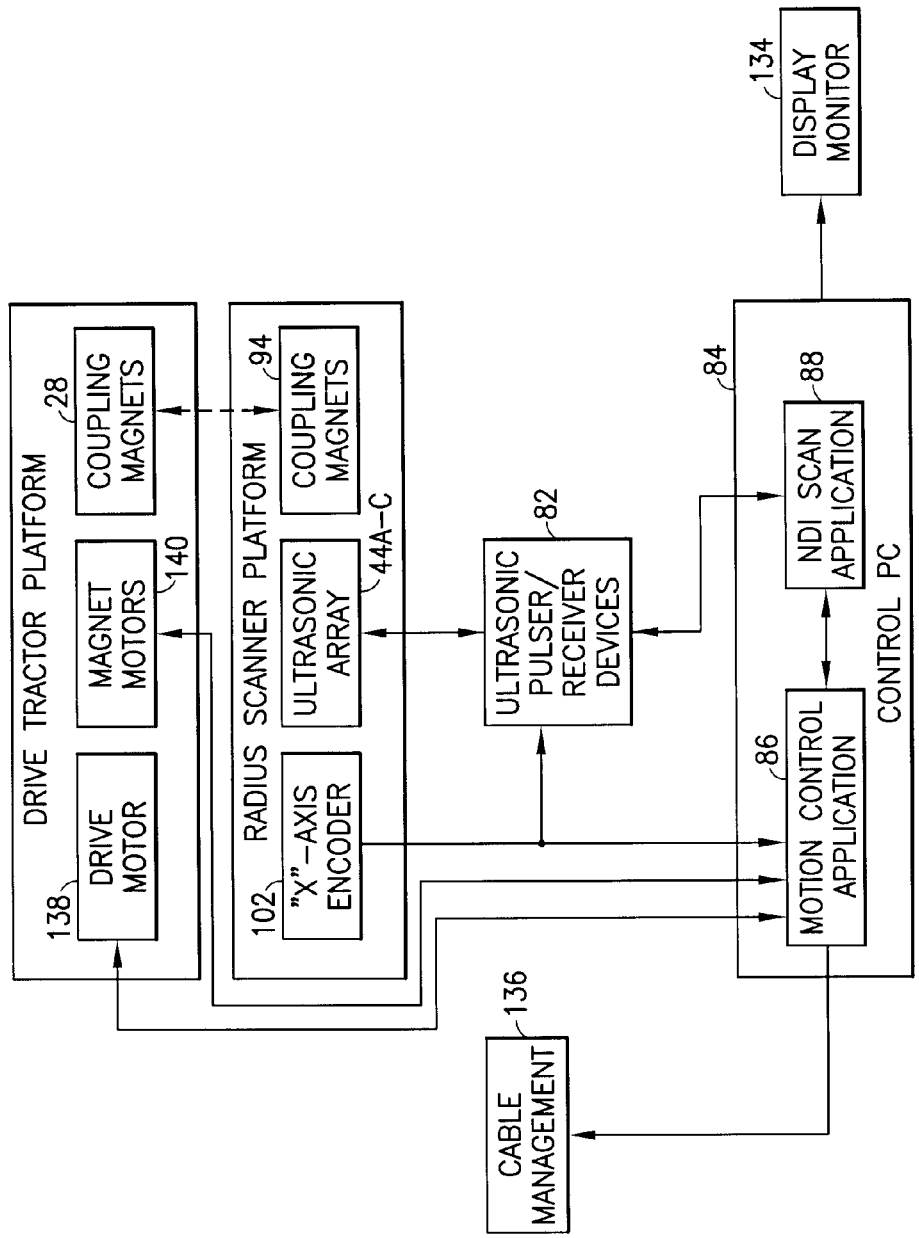
FIG. 17 is a block diagram showing a control system in accordance with one embodiment.

FIG. 17 is a block diagram showing a control system in accordance with one embodiment. The control system comprises a ground-based computer 84 programmed with motion control application software 86 and NDI scan application software 88. The control computer 84 is connected to the drive tractor platform (previously referred to as a "tractor vehicle") and to the radius scanner by flexible electrical cables that connect to an electronics box (not shown). The electronics box contains the system power supplies and integrates all the scanner control connections and provides an interface between the computer, drive tractor, and radius scanner.

The computer 84 may comprise a general-purpose computer programmed with motion control application software 86 comprising respective software modules for controlling drive motor 138 and magnet vertical positioning motors 140 onboard the drive tractor platform. The magnet motors 140 displace the tractor coupling magnets 28 as disclosed in U.S. patent application Ser. No. 13/313,267.

The motion control application software 86 also controls a motor of a cable management system 136. The cable management system 136 consists of two sets of motorized wheels that respectively grip the cables connecting the operations control center to the tractor and radius scanner. The motor of the cable management system is under computer control, which synchronizes the cables with the movement of the radius scanner and the tractor, extending or retracting the cables as appropriate.

In accordance with one embodiment, the encoded data from encoder 102 is received by three ultrasonic pulser/receiver devices 82, which in turn send those encoder pulses to the NDI scan software 88. The NDI scanning software application 88 uses these pulses to position the scan data in the proper location on a display monitor 134. An offset for each array is used for final display. The offset corresponds to the physical distance between the arrays in the array housing. The pixel columns having values derived from data acquired in the same scan plane by each array are aligned as one in the final display.

The NDI scan application 88 includes ultrasonic data acquisition and display software that controls the ultrasonic pulser/receiver devices 82. The ultrasonic pulser/receiver devices 82 in turn send pulses to and receive return signals from the ultrasonic transducer arrays 44a-c. The NDI scan application software 88 controls all details of the scan data and the display of data. The pulser/receiver devices 82 correlate the acquired ultrasonic data with the X-position information.

One embodiment of the control system depicted in FIG. 17 has the ability to provide meaningful distance information in a final C-scan. The C-scan presentation provides a plan-type view of the location and size of part features. The plane of the image is parallel to the scan pattern of the transducer arrays. In a C-scan, there is distance information shown in the display. The distance information is found along the horizontal and vertical axes (or rulers) of the display. Individual pixels make up the C-scan. The width of the pixel directly corresponds to the resolution of the dimensional encoder 102 running along the horizontal axis of the part. However, the distance in the vertical direction must correlate to the distance between the beams directed at different targets in a scan plane. Set targets are provided along each radius arc length. Since groups of beams are hitting each target, the distance between the groups of beams corresponds to the physical distance between the targets. Eventually, operators will have to make area measurements of flaws that might show up in the C-scan. This would be hard to do if all the beams were displayed in the C-scan because multiple beams would be hitting the same target and there would be redundancy in the area measurements. However, if a selected focal law is used from each group of beams, the distance between the theoretical targets directly correlates to the height of the C-scan pixels. Optionally, this beam selection can be done during post-processing after the part has been scanned. The NDI scan application includes data analysis software which is used to determine the best return signals according to the method previously described. The best return signals may be derived from front surface echoes, from back surface echoes, by calculating a weighted function of two or more front surface echoes, by recording all echoes within an internal gate, or any other suitable means.

While various embodiments have been described, it will be understood by those skilled in the art that various changes may be made and equivalents may be substituted for elements thereof without departing from the scope of the teachings herein. In addition, many modifications may be made to adapt a particular situation to the teachings herein without departing from the scope thereof. Therefore it is intended that scope of the claims set forth hereinafter not be limited to the disclosed embodiments.

As used in the claims, the term "computer system" should be construed broadly to encompass a system having at least one computer or processor, and which may have two or more interconnected computers or processors.

The method claims set forth hereinafter should not be construed to require that the steps recited therein be performed in alphabetical order or in the order in which they are recited. Nor should they be construed to exclude any portions of two or more steps being performed concurrently.

The invention claimed is:

1. A method for inspecting a portion of a part having a surface of unknown radiused shape, the method comprising:
    (a) positioning and orienting a linear array of ultrasonic transducer elements at a location whereat the linear array can be operated to transmit focused and steered ultrasonic beams in a scan plane that will impinge on a radiused surface of the part having a curved concave profile in the scan plane;
    (b) while the linear array is stationary at said location, electrically pulsing the ultrasonic transducer elements of different apertures of the linear array using phasing to transmit a sequence of successive focused and steered ultrasonic beams directed toward one and the same target location on the radiused surface, each focused and steered ultrasonic beam being formed by pulsing the ultrasonic transducer elements of a respective one of the different apertures to produce a respective focused ultrasonic beam having a respective different steering angle;
    (c) while the linear array is stationary at said location and after the ultrasonic transducer elements making up each aperture have been pulsed, forming electrical signals from the ultrasonic transducer elements of the respective aperture into a respective return signal representing a respective echo returned to the respective aperture from the target location on the radiused surface following electrical pulsing of the ultrasonic transducer elements of the respective aperture;
    (d) processing said return signals to derive respective values of a parameter characterizing said return signals from the target location; and
    (e) selecting one of said respective parameter values that satisfies a first condition,
    wherein steps (b) through (e) are repeated for each of a multiplicity of target locations disposed on the radiused surface at spaced intervals along a scan line in the scan plane.

2. The method as recited in claim 1, wherein said parameter is amplitude and said first condition is having the greatest amplitude.

3. The method as recited in claim 1, further comprising displaying a pixel having a value which is a function of at least said selected parameter value.

4. The method as recited in claim 1, further comprising:
    selecting another of said respective parameter values that satisfies said first condition or a second condition; and
    displaying a pixel having a value which is a function of at least said one and said another selected parameter values.

5. The method as recited in claim 1, further comprising supplying fluid acoustic couplant into a space between the linear array and the part, wherein step (d) comprises applying respective gains to said respective return signals, said gains being selected to compensate for different amounts of energy loss caused by transmission inefficiency at higher angles, said respective gains being a function of distance of travel of each echo through said fluid acoustic couplant.

* * * * *